US010370418B2

(12) United States Patent
Thelen et al.

(10) Patent No.: US 10,370,418 B2
(45) Date of Patent: Aug. 6, 2019

(54) ENGINEERED MICROORGANISMS HAVING RESISTANCE TO IONIC LIQUIDS

(71) Applicant: Lawrence Livermore National Security, LLC, Livermore, CA (US)

(72) Inventors: Michael P. Thelen, Danville, CA (US); Douglas A. Higgins, Point Pleasant, NJ (US); Thomas L. Ruegg, Berkeley, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 24 days.

(21) Appl. No.: 14/717,962

(22) Filed: May 20, 2015

(65) Prior Publication Data

US 2016/0090405 A1 Mar. 31, 2016

Related U.S. Application Data

(60) Provisional application No. 62/001,014, filed on May 20, 2014.

(51) Int. Cl.
| C12N 1/14 | (2006.01) |
| C12N 1/16 | (2006.01) |
| C12N 1/20 | (2006.01) |
| C12P 7/10 | (2006.01) |
| C07K 14/255 | (2006.01) |
| C07K 14/395 | (2006.01) |

(52) U.S. Cl.
CPC .......... *C07K 14/255* (2013.01); *C07K 14/395* (2013.01); *C12N 1/14* (2013.01); *C12N 1/16* (2013.01); *C12N 1/20* (2013.01); *C12P 7/10* (2013.01); *C12P 2203/00* (2013.01); *Y02E 50/16* (2013.01)

(58) Field of Classification Search
None
See application file for complete search history.

(56) References Cited

U.S. PATENT DOCUMENTS

| 9,290,768 B2* | 3/2016 | Ruegg | C12N 15/70 |
| 2007/0155000 A1* | 7/2007 | Nilsson | C12N 9/0006 435/161 |
| 2013/0302868 A1* | 11/2013 | Dundon | C07K 14/395 435/160 |
| 2015/0361476 A1* | 12/2015 | Simon | C07K 14/395 435/78 |

OTHER PUBLICATIONS

Santiviago et al., "The *Salmonella enterica* sv. Typhimurium smvA, yddG and ompD (porin) genes are required for the efficient efflux of methyl viologen", Molecular Microbiology, vol. 46, No. 3, pp. 687-698, 2002.*
Guo et al., "Protein tolerance to random amino acid change", Proceedings of the National Academy of Sciences USA, vol. 101, No. 25, pp. 9205-9210, 2004.*

* cited by examiner

*Primary Examiner* — Richard C Ekstrom
(74) *Attorney, Agent, or Firm* — Robin C. Chiang; Lawrence Berkeley National Laboratory

(57) ABSTRACT

The present invention provides for a method of genetically modifying microorganisms to enhance resistance to ionic liquids using a yeast Major Facilitator Superfamily (MFS), or a *Salmonella* MFS SmvA Pump or SmvR Regulator, a Small Multidrug Resistance Family (SMR), or *Saccharomyces cerevisiae* YDR090C, polypeptide, host cells genetically modified in accordance with the methods, and methods of using the host cells in a reaction comprising biomass that has been pretreated with ionic liquids.

11 Claims, 4 Drawing Sheets

Specification includes a Sequence Listing.

SEQUENCE LISTING

```
<160> NUMBER OF SEQ ID NOS: 38

<210> SEQ ID NO 1
<211> LENGTH: 495
```

<212> TYPE: PRT
<213> ORGANISM: Salmonella typhimurium

<400> SEQUENCE: 1

```
Met Phe Arg Gln Trp Leu Thr Leu Val Ile Ile Val Leu Val Tyr Ile
1               5                   10                  15

Pro Val Ala Ile Asp Ala Thr Val Leu His Val Ala Ala Pro Thr Leu
            20                  25                  30

Ser Met Thr Leu Gly Ala Ser Gly Asn Glu Leu Leu Trp Ile Ile Asp
        35                  40                  45

Ile Tyr Ser Leu Val Met Ala Gly Met Val Leu Pro Met Gly Ala Leu
    50                  55                  60

Gly Asp Arg Ile Gly Phe Lys Arg Leu Leu Met Leu Gly Gly Thr Leu
65                  70                  75                  80

Phe Gly Leu Ala Ser Leu Ala Ala Ala Phe Ser His Thr Ala Ser Trp
                85                  90                  95

Leu Ile Ala Thr Arg Val Leu Leu Ala Ile Gly Ala Ala Met Ile Val
            100                 105                 110

Pro Ala Thr Leu Ala Gly Ile Arg Ala Thr Phe Cys Glu Glu Lys His
        115                 120                 125

Arg Asn Met Ala Leu Gly Val Trp Ala Ala Val Gly Ser Gly Gly Ala
    130                 135                 140

Ala Phe Gly Pro Leu Ile Gly Gly Ile Leu Leu Glu His Phe Tyr Trp
145                 150                 155                 160

Gly Ser Val Phe Leu Ile Asn Val Pro Ile Val Leu Val Val Met Gly
                165                 170                 175

Leu Thr Ala Arg Tyr Val Pro Arg Gln Ala Gly Arg Arg Asp Gln Pro
            180                 185                 190

Leu Asn Leu Gly His Ala Val Met Leu Ile Ile Ala Ile Leu Leu Leu
        195                 200                 205

Val Tyr Ser Ala Lys Thr Ala Leu Lys Gly His Leu Ser Leu Trp Val
    210                 215                 220

Ile Ser Phe Thr Leu Leu Thr Gly Ala Leu Leu Leu Gly Leu Phe Ile
225                 230                 235                 240

Arg Thr Gln Leu Ala Thr Ser Arg Pro Met Ile Asp Met Arg Leu Phe
                245                 250                 255

Thr His Arg Ile Ile Leu Ser Gly Val Val Met Ala Met Thr Ala Met
            260                 265                 270

Ile Thr Leu Val Gly Phe Glu Leu Leu Met Ala Gln Glu Leu Gln Phe
        275                 280                 285

Val His Gly Leu Ser Pro Tyr Glu Ala Gly Val Phe Met Leu Pro Val
    290                 295                 300

Met Val Ala Ser Gly Phe Ser Gly Pro Ile Ala Gly Val Leu Val Ser
305                 310                 315                 320

Arg Leu Gly Leu Arg Leu Val Ala Thr Gly Gly Met Ala Leu Ser Ala
                325                 330                 335

Leu Ser Phe Tyr Gly Leu Ala Met Thr Asp Phe Ser Thr Gln Gln Trp
            340                 345                 350

Gln Ala Trp Gly Leu Met Ala Leu Gly Phe Ser Ala Ala Ser Ala
    355                 360                 365

Leu Leu Ala Ser Thr Ser Ala Ile Met Ala Ala Pro Ala Glu Lys
370                 375                 380

Ala Ala Ala Ala Gly Ala Ile Glu Thr Met Ala Tyr Glu Leu Gly Ala
385                 390                 395                 400
```

```
Gly Leu Gly Ile Ala Ile Phe Gly Leu Leu Ser Arg Ser Phe Ser
                405                 410                 415

Ala Ser Ile Arg Leu Pro Ala Gly Leu Glu Ala Gln Glu Ile Ala Arg
            420                 425                 430

Ala Ser Ser Ser Met Gly Glu Ala Val Gln Leu Ala Asn Ser Leu Pro
        435                 440                 445

Pro Thr Gln Gly Gln Ala Ile Leu Asp Ala Ala Arg His Ala Phe Ile
    450                 455                 460

Trp Ser His Ser Val Ala Leu Ser Ser Ala Gly Ser Met Leu Leu Leu
465                 470                 475                 480

Leu Ala Val Gly Met Trp Phe Ser Leu Ala Lys Ala Gln Arg Arg
                485                 490                 495

<210> SEQ ID NO 2
<211> LENGTH: 192
<212> TYPE: PRT
<213> ORGANISM: Salmonella typhimurium

<400> SEQUENCE: 2

Met Ser Tyr Leu Asn Arg Asp Glu Arg Arg Glu Val Ile Leu Gln Ala
1               5                   10                  15

Ala Met Arg Val Ala Leu Ala Glu Gly Phe Ala Ala Met Thr Val Arg
            20                  25                  30

Arg Ile Ala Ser Glu Ala Asp Val Ala Ala Gly Gln Val His His His
        35                  40                  45

Phe Ser Ser Ala Gly Glu Leu Lys Ala Leu Ala Phe Val His Leu Ile
    50                  55                  60

Arg Thr Leu Leu Asp Ala Gly Gln Val Pro Pro Pro Ala Thr Trp Arg
65                  70                  75                  80

Ala Arg Leu His Ala Met Leu Gly Ser Glu Asp Gly Gly Phe Glu Pro
                85                  90                  95

Tyr Ile Lys Leu Trp Arg Glu Ala Gln Ile Leu Ala Asp Arg Asp Pro
            100                 105                 110

His Ile Arg Asp Ala Tyr Leu Leu Thr Met Gln Met Trp His Glu Glu
        115                 120                 125

Thr Val Thr Ile Ile Glu Gln Gly Lys Gln Ala Gly Glu Phe Thr Phe
    130                 135                 140

Thr Ala Asn Ala Thr Asp Ile Ala Trp Arg Leu Ile Ala Leu Val Cys
145                 150                 155                 160

Gly Leu Asp Gly Met Tyr Val Leu Gly Ile Pro Glu Met Ala Asp Pro
                165                 170                 175

Ala Phe Lys Phe His Leu Asp Arg Met Ile Thr Leu Glu Leu Phe Ala
            180                 185                 190

<210> SEQ ID NO 3
<211> LENGTH: 109
<212> TYPE: PRT
<213> ORGANISM: Bacillus licheniformis

<400> SEQUENCE: 3

Met Arg Trp Gly Ser Val Ile Leu Ala Ala Leu Phe Glu Ile Gly Trp
1               5                   10                  15

Val Met Gly Leu Lys His Ala Asp Ser Ala Leu Glu Trp Ile Cys Thr
            20                  25                  30

Ala Ala Ala Val Val Met Ser Phe Tyr Ile Leu Val Lys Ala Gly Glu
        35                  40                  45
```

Lys Leu Pro Val Gly Thr Val Tyr Ala Val Phe Thr Gly Leu Gly Thr
    50                  55                  60

Ala Gly Thr Val Val Cys Glu Ile Ala Leu Phe Asn Glu Pro Ala Asn
65                  70                  75                  80

Ile Ala Lys Leu Ala Leu Ile Gly Val Leu Leu Cys Gly Val Ile Gly
                85                  90                  95

Leu Lys Leu Val Thr Asn Glu Glu Lys Gly Glu Ala Ser
            100                 105

<210> SEQ ID NO 4
<211> LENGTH: 104
<212> TYPE: PRT
<213> ORGANISM: Bacillus licheniformis

<400> SEQUENCE: 4

Met Glu Trp Ile Cys Leu Ile Ala Ala Gly Ile Leu Glu Met Leu Gly
1               5                   10                  15

Val Thr Met Met Asn Gln Phe His Lys Asp Lys Arg Val Arg Trp Ile
            20                  25                  30

Phe Leu Leu Ile Ile Gly Phe Ala Ala Ser Phe Phe Leu Leu Ser Leu
        35                  40                  45

Ala Met Glu Thr Leu Pro Met Gly Thr Ala Tyr Ala Val Trp Thr Gly
    50                  55                  60

Ile Gly Thr Val Gly Gly Ala Leu Val Gly Ile Leu Phe Tyr Gly Glu
65                  70                  75                  80

Pro Lys Asp Gly Lys Arg Ile Phe Phe Ile Ala Leu Ile Leu Gly Ser
                85                  90                  95

Ala Val Gly Leu Lys Leu Ile Ser
            100

<210> SEQ ID NO 5
<211> LENGTH: 114
<212> TYPE: PRT
<213> ORGANISM: Bacillus cereus

<400> SEQUENCE: 5

Met Lys Asn Arg Ala Trp Leu Tyr Val Ile Leu Thr Cys Ile Phe Glu
1               5                   10                  15

Ile Phe Trp Val Phe Gly Phe Asn Thr Ala Asp Thr Trp Trp His Trp
            20                  25                  30

Ile Ile Ile Leu Gly Val Ile Ala Val Asp Phe His Phe Leu Ser Lys
        35                  40                  45

Ala Cys Glu His Leu Ala Thr Gly Thr Val Tyr Ala Ile Phe Ala Gly
    50                  55                  60

Ala Gly Thr Val Gly Thr Phe Leu Met Asp Val Phe Leu Phe Gly Gly
65                  70                  75                  80

Ser Phe Ser Val Gly Lys Leu Phe Phe Ile Val Met Val Val Ala Gly
                85                  90                  95

Val Ile Gly Leu Lys Leu Ala Asp Asn Lys Glu Glu Ser Val Glu Gly
            100                 105                 110

Ala Ala

<210> SEQ ID NO 6
<211> LENGTH: 104
<212> TYPE: PRT
<213> ORGANISM: Bacillus cereus

```
<400> SEQUENCE: 6

Met Gly Trp Phe Phe Val Phe Cys Ala Ala Ile Ser Glu Ile Val Gly
1               5                   10                  15

Val Ile Gly Leu Lys Met Tyr Ser Lys Asp Lys Thr Leu Ala Asn Gly
            20                  25                  30

Ala Leu Tyr Ile Gly Gly Phe Ala Thr Ser Phe Ala Phe Leu Tyr Thr
        35                  40                  45

Ser Phe Leu Phe Leu Gln Val Ser Val Ala Tyr Ala Val Trp Ile Gly
    50                  55                  60

Ile Gly Thr Ala Gly Ala Val Leu Leu Asn Met Phe Leu Phe Gly Glu
65                  70                  75                  80

Ser Lys Ser Lys Ala Arg Ile Ile Ser Val Ala Leu Ile Val Cys Gly
            85                  90                  95

Val Thr Gly Leu Lys Ala Leu Ser
            100

<210> SEQ ID NO 7
<211> LENGTH: 192
<212> TYPE: PRT
<213> ORGANISM: Bacillus cereus

<400> SEQUENCE: 7

Met Met Asn Lys Lys Glu Lys Ile Val Tyr Ala Ala Ile Glu Val Phe
1               5                   10                  15

Gln Glu Lys Gly Val Glu Lys Thr Lys Ile Ser Asp Ile Val Lys Leu
            20                  25                  30

Ala Gly Ile Ala Gln Gly Thr Phe Tyr Leu Tyr Phe Pro Ser Lys Leu
        35                  40                  45

Ser Val Met Pro Ala Ile Ala Gl

```
                20                  25                  30
Leu Ser Leu Tyr Gln Tyr Leu Gln Cys Leu Tyr Val Val Lys Glu Glu
        35                  40                  45

Glu Lys Ile Val Gly Val Ala Gly Leu His Val Leu Gly Glu Asp Leu
    50                  55                  60

Ala Glu Val Arg Ser Leu Val Val Ser His Thr Tyr Ala Gly Lys Gly
65                  70                  75                  80

Ile Gly Arg Met Leu Val Asn His Val Ile Asn Glu Ala Ala Lys Ile
                85                  90                  95

Lys Val Ser Arg Val Ile Ser Leu Thr Tyr Glu Thr Glu Phe Phe Gln
            100                 105                 110

Lys Cys Gly Phe Asp Phe Val Asn Arg Asp Ala Leu Pro Glu Lys Val
        115                 120                 125

Trp Ile Asp Cys Arg His Cys Pro Lys Val Asp Tyr Cys Asp Glu Val
    130                 135                 140

Ala Met Ile Arg Tyr Val Gly
145                 150

<210> SEQ ID NO 9
<211> LENGTH: 117
<212> TYPE: PRT
<213> ORGANISM: Bacillus thuringiensis

<400> SEQUENCE: 9

Met Arg Gly Met Lys Asn Arg Ala Trp Leu Tyr Val Ile Leu Thr Cys
1               5                   10                  15

Ile Phe Glu Ile Phe Trp Val Phe Gly Phe Asn Thr Ala Asp Thr Trp
                20                  25                  30

Trp His Trp Ile Ile Ile Leu Gly Val Ile Ala Val Asp Phe His Phe
            35                  40                  45

Leu Ser Lys Ala Cys Glu His Leu Ala Thr Gly Thr Val Tyr Ala Val
    50                  55                  60

Phe Ala Gly Ala Gly Thr Val Gly Thr Phe Leu Met Asp Val Phe Leu
65                  70                  75                  80

Phe Gly Gly Ser Phe Ser Ala Gly Lys Leu Phe Phe Ile Leu Met Val
                85                  90                  95

Val Ala Gly Val Ile Gly Leu Lys Leu Ala Asp Asn Lys Glu Glu Thr
            100                 105                 110

Val Glu Gly Ala Ala
        115

<210> SEQ ID NO 10
<211> LENGTH: 104
<212> TYPE: PRT
<213> ORGANISM: Bacillus thuringiensis

<400> SEQUENCE: 10

Met Gly Trp Phe Phe Val Phe Cys Ala Ala Ile Ser Glu Ile Val Gly
1               5                   10                  15

Val Ile Gly Leu Lys Met Tyr Ser Lys Asp Lys Thr Leu Ala Asn Gly
                20                  25                  30

Ala Ile Tyr Ile Gly Gly Phe Ala Thr Ser Phe Ala Leu Tyr Thr
            35                  40                  45

Ser Phe Leu Phe Leu Gln Val Ser Val Ala Tyr Ala Val Trp Ile Gly
    50                  55                  60

Ile Gly Thr Ala Gly Ala Val Leu Leu Asn Met Phe Leu Phe Gly Glu
```

```
                65                  70                  75                  80
Ser Lys Ser Lys Ala Arg Ile Ile Ser Val Phe Leu Ile Val Cys Gly
                    85                  90                  95

Val Thr Gly Leu Lys Ala Leu Ser
                100

<210> SEQ ID NO 11
<211> LENGTH: 192
<212> TYPE: PRT
<213> ORGANISM: Bacillus thuringiensis

<400> SEQUENCE: 11

Met Met Asn Lys Lys Glu Lys Ile Val Tyr Ala Ala Ile Glu Val Phe
1               5                   10                  15

Gln Glu Lys Gly Val Glu Lys Thr Lys Ile Ser Asp Ile Val Lys Leu
                20                  25                  30

Ala Gly Ile Ala Gln Gly Thr Phe Tyr Leu Tyr Phe Pro Ser Lys Leu
            35                  40                  45

Ser Val Met Pro Ala Ile Ala Glu Val Met Val Glu Lys Met Ile Leu
        50                  55                  60

Ala Val Lys Glu Lys Val Gln Lys Asp Val Pro Phe Ser Asn Lys Val
65                  70                  75                  80

Ala Gln Val Ile Asp Ala Val Phe His Phe Ile Glu Glu Tyr Arg Glu
                85                  90                  95

Ile Gln Ala Leu Met Tyr Ala Gly Leu Ala Ser Thr Glu His Ile Lys
                100                 105                 110

Glu Trp Glu Ala Val Tyr Glu Pro Leu Tyr Met Trp Leu Ser Glu Phe
            115                 120                 125

Leu Ser Glu Ala Lys Glu Ala Gly Glu Ile Arg Asp Ser Val His Ala
        130                 135                 140

Glu Arg Thr Ala Lys Leu Phe Ile Ala Leu Val Glu Ser Ala Ala Glu
145                 150                 155                 160

Gln Val Tyr Leu Tyr Asp His Lys Asp Asp Glu Gln Val Glu Leu Gln
                165                 170                 175

Lys Ala Glu Val Leu Asp Phe Leu Thr His Ala Leu His Ile Lys Lys
            180                 185                 190

<210> SEQ ID NO 12
<211> LENGTH: 145
<212> TYPE: PRT
<213> ORGANISM: Bacillus thuringiensis

<400> SEQUENCE: 12

Met Thr Ser Asp Val Lys Glu Ile Tyr Asn Leu Ile Glu Val Tyr Ala
1               5                   10                  15

Lys Glu Gly Val Val Leu Pro Arg Ser Leu Leu Ser Leu Tyr Gln Tyr
                20                  25                  30

Leu Gln Cys Leu Tyr Val Met Lys Glu Asp Glu Arg Ile Val Gly Val
            35                  40                  45

Ala Gly Leu His Val Leu Gly Glu Asp Leu Ala Glu Ile Arg Ser Leu
        50                  55                  60

Val Val Ser His Thr Tyr Ala Gly Lys Gly Ile Gly Arg Met Leu Val
65                  70                  75                  80

Asn His Val Met Glu Glu Ala Thr Lys Ile Asn Val Arg Arg Val Ile
                85                  90                  95

Ser Leu Thr Tyr Glu Thr Val Phe Phe Gln Lys Cys Gly Phe Asp Phe
```

```
            100                 105                 110
Val Asn Lys Glu Thr Leu Pro Glu Lys Val Trp Ile Asp Cys Arg His
            115                 120                 125
Cys Pro Lys Val Asp Tyr Cys Asp Glu Val Ala Met Val Arg Tyr Val
            130                 135                 140
Gly
145

<210> SEQ ID NO 13
<211> LENGTH: 110
<212> TYPE: PRT
<213> ORGANISM: Bacillus cereus

<400> SEQUENCE: 13

Met Ala Trp Ile Tyr Val Ile Leu Ala Gly Ile Ile Glu Ile Phe Trp
1               5                   10                  15
Val Ile Gly Leu Lys His Ala Glu Ala Pro Leu Glu Trp Ala Gly Val
            20                  25                  30
Ala Leu Leu Ile Thr Ile Ser Phe Val Leu Leu Phe Arg Ala Tyr Lys
        35                  40                  45
Asp Leu Pro Val Gly Thr Val Tyr Ala Val Phe Thr Gly Ile Gly Ala
    50                  55                  60
Gly Gly Ile Val Leu Thr Glu Ile Phe Val Phe Gly Glu Pro Phe Ser
65                  70                  75                  80
Ile Val Lys Val Leu Leu Ile Gly Leu Ile Phe Phe Gly Val Ile Gly
                85                  90                  95
Leu Lys Arg Val Thr Glu Glu Lys Glu Ala Lys Glu Ala Ala
            100                 105                 110

<210> SEQ ID NO 14
<211> LENGTH: 104
<212> TYPE: PRT
<213> ORGANISM: Bacillus cereus

<400> SEQUENCE: 14

Met Ala Trp Val Phe Leu Ile Leu Ala Gly Ile Cys Glu Ile Ile Gly
1               5                   10                  15
Val Leu Phe Met Lys Val Ala Thr Glu Lys Lys Gly Trp Ala Pro Lys
            20                  25                  30
Val Ile Leu Ile Ala Asn Phe Gly Val Ser Phe Phe Leu Ser Leu
        35                  40                  45
Ala Met Asn Thr Leu Pro Met Gly Thr Ala Tyr Ala Ile Trp Thr Gly
    50                  55                  60
Ile Gly Thr Ala Gly Ser Ala Leu Leu Gly Ile Leu Ile Phe Arg Glu
65                  70                  75                  80
Ser Ala Asp Trp Arg Arg Leu Ala Phe Leu Ser Cys Ile Leu Cys Gly
                85                  90                  95
Ala Val Gly Leu Lys Leu Leu Ser
            100

<210> SEQ ID NO 15
<211> LENGTH: 191
<212> TYPE: PRT
<213> ORGANISM: Bacillus cereus

<400> SEQUENCE: 15

Met Thr Ala Asn Arg Ile Lys Ala Val Ala Leu Ser His Phe Ala Arg
1               5                   10                  15
```

Tyr Gly Tyr Glu Gly Thr Ser Leu Ala Asn Ile Ala Gln Glu Val Gly
            20                  25                  30

Ile Lys Lys Pro Ser Ile Tyr Ala His Phe Lys Gly Lys Glu Glu Leu
        35                  40                  45

Tyr Phe Thr Cys Leu Glu Ser Ala Leu Gln Lys Asp Leu Gln Ser Phe
    50                  55                  60

Thr Gly Asp Ile Glu Lys Phe Ser Asn Ser Thr Glu Glu Leu Leu
65                  70                  75                  80

Leu Gln Leu Leu Lys Gly Tyr Ala Lys Arg Phe Gly Glu Ser Glu Glu
                85                  90                  95

Ser Met Phe Trp Leu Arg Thr Ser Tyr Phe Pro Pro Asp Ala Phe Arg
            100                 105                 110

Glu Gln Ile Ile Asn Lys Ala Asn Val His Ile Glu Asn Val Gly Lys
        115                 120                 125

Leu Leu Phe Pro Val Phe Lys Arg Ala Ser Glu Gln Asp Glu Leu His
    130                 135                 140

Asn Ile Glu Val Lys Asp Ala Leu Glu Ala Phe Leu Cys Leu Leu Asp
145                 150                 155                 160

Gly Leu Met Val Glu Leu Leu Tyr Ala Gly Leu Asn Arg Phe Glu Thr
                165                 170                 175

Arg Leu Asp Ala Ser Trp Lys Val Phe Trp Arg Gly Leu Ser Asn
            180                 185                 190

<210> SEQ ID NO 16
<211> LENGTH: 110
<212> TYPE: PRT
<213> ORGANISM: Bacillus thuringiensis

<400> SEQUENCE: 16

Met Ala Trp Ile Tyr Val Ile Ile Ala Gly Ile Ile Glu Ile Phe Trp
1               5                   10                  15

Val Ile Gly Leu Lys Lys Ala Glu Ala Pro Leu Glu Trp Ala Gly Val
            20                  25                  30

Ala Leu Leu Ile Thr Ile Ser Phe Val Leu Leu Phe Arg Ala Tyr Lys
        35                  40                  45

Asp Leu Pro Val Gly Thr Val Tyr Ala Val Phe Thr Gly Ile Gly Ala
    50                  55                  60

Gly Gly Ile Val Leu Thr Glu Ile Phe Ile Phe Gly Glu Pro Phe Ser
65                  70                  75                  80

Ile Val Lys Val Leu Leu Ile Gly Leu Ile Phe Phe Gly Val Ile Gly
                85                  90                  95

Leu Lys Arg Val Thr Glu Glu Lys Glu Ala Lys Glu Ala Ala
            100                 105                 110

<210> SEQ ID NO 17
<211> LENGTH: 104
<212> TYPE: PRT
<213> ORGANISM: Bacillus thuringiensis

<400> SEQUENCE: 17

Met Ala Trp Val Phe Leu Ile Leu Ala Gly Ile Cys Glu Ile Ile Gly
1               5                   10                  15

Val Leu Phe Met Lys Val Ala Thr Glu Lys Lys Gly Trp Ala Pro Lys
            20                  25                  30

Val Ile Leu Ile Ala Asn Phe Gly Val Ser Phe Phe Leu Ser Leu
        35                  40                  45

```
Ala Met Asn Thr Leu Pro Met Gly Thr Ala Tyr Ala Ile Trp Thr Gly
    50                  55                  60

Ile Gly Thr Ala Gly Ser Ala Leu Leu Gly Ile Leu Ile Phe Arg Glu
65                  70                  75                  80

Ser Ala Asp Trp Arg Arg Leu Ala Phe Leu Ser Cys Ile Leu Cys Gly
                85                  90                  95

Ala Val Gly Leu Lys Leu Leu Ser
            100

<210> SEQ ID NO 18
<211> LENGTH: 193
<212> TYPE: PRT
<213> ORGANISM: Bacillus thuringiensis

<400> SEQUENCE: 18

Met Lys Met Thr Ala Asn Arg Ile Lys Ala Val Ala Leu Ser His Phe
1               5                   10                  15

Ala Arg Tyr Gly Tyr Glu Gly Thr Ser Leu Ala Asn Ile Ala Gln Glu
            20                  25                  30

Val Gly Ile Lys Lys Pro Ser Ile Tyr Ala His Phe Lys Gly Lys Glu
        35                  40                  45

Glu Leu Tyr Phe Ile Cys Leu Glu Ser Ala Leu Gln Lys Asp Leu Gln
    50                  55                  60

Ser Phe Thr Gly Asp Ile Glu Ser Phe Ser Asn Ser Ser Thr Glu Glu
65                  70                  75                  80

Leu Leu Leu Lys Leu Leu Lys Gly Tyr Ala Lys Arg Phe Gly Glu Ser
                85                  90                  95

Glu Glu Ser Met Phe Trp Leu Arg Thr Ser Tyr Phe Pro Pro Asp Ala
            100                 105                 110

Phe Arg Glu Gln Ile Ile Asn Lys Ala Asn Val His Ile Glu Asn Val
        115                 120                 125

Gly Lys Leu Leu Phe Pro Val Phe Lys Arg Ala Ser Glu Gln Asp Glu
    130                 135                 140

Leu His Asn Ile Glu Val Lys Asp Ala Leu Glu Ala Phe Leu Cys Leu
145                 150                 155                 160

Leu Asp Gly Leu Met Val Glu Leu Leu Tyr Ala Gly Leu Asn Arg Phe
                165                 170                 175

Glu Thr Arg Leu Asp Ala Ser Trp Lys Val Phe Trp Arg Gly Leu Ser
            180                 185                 190

Asn

<210> SEQ ID NO 19
<211> LENGTH: 110
<212> TYPE: PRT
<213> ORGANISM: Escherichia coli

<400> SEQUENCE: 19

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly Ile Ala Tyr Ala Ile Trp Ser
    50                  55                  60
```

Gly Val Gly Ile Val Leu Ile Ser Leu Leu Ser Trp Gly Phe Phe Gly
65                  70                  75                  80

Gln Arg Leu Asp Leu Pro Ala Ile Ile Gly Met Met Leu Ile Cys Ala
                85                  90                  95

Gly Val Leu Ile Ile Asn Leu Leu Ser Arg Ser Thr Pro His
            100                 105                 110

<210> SEQ ID NO 20
<211> LENGTH: 105
<212> TYPE: PRT
<213> ORGANISM: Escherichia coli

<400> SEQUENCE: 20

Met Ser Trp Ile Ile Leu Val Ile Ala Gly Leu Leu Glu Val Val Trp
1               5                   10                  15

Ala Val Gly Leu Lys Tyr Thr His Gly Phe Ser Arg Leu Thr Pro Ser
                20                  25                  30

Val Ile Thr Val Thr Ala Met Ile Val Ser Met Ala Leu Leu Ala Trp
            35                  40                  45

Ala Met Lys Ser Leu Pro Val Gly Thr Ala Tyr Ala Val Trp Thr Gly
    50                  55                  60

Ile Gly Ala Val Gly Ala Ala Ile Thr Gly Ile Val Leu Leu Gly Glu
65                  70                  75                  80

Ser Ala Asn Pro Met Arg Leu Ala Ser Leu Ala Leu Ile Val Leu Gly
                85                  90                  95

Ile Ile Gly Leu Lys Leu Ser Thr His
            100                 105

<210> SEQ ID NO 21
<211> LENGTH: 543
<212> TYPE: PRT
<213> ORGANISM: Saccharomyces cerevisiae

<400> SEQUENCE: 21

Met Lys Ser Thr Leu Ser Leu Thr Leu Cys Val Ile Ser Leu Leu Leu
1               5                   10                  15

Thr Leu Phe Leu Ala Ala Leu Asp Ile Val Ile Val Val Thr Leu Tyr
                20                  25                  30

Asp Thr Ile Gly Ile Lys Phe His Asp Phe Gly Asn Ile Gly Trp Leu
            35                  40                  45

Val Thr Gly Tyr Ala Leu Ser Asn Ala Val Phe Met Leu Leu Trp Gly
    50                  55                  60

Arg Leu Ala Glu Ile Leu Gly Thr Lys Glu Cys Leu Met Ile Ser Val
65                  70                  75                  80

Ile Val Phe Glu Ile Gly Ser Leu Ile Ser Ala Leu Ser Asn Ser Met
                85                  90                  95

Ala Thr Leu Ile Ser Gly Arg Val Val Ala Gly Phe Gly Ser Gly
            100                 105                 110

Ile Glu Ser Leu Ala Phe Val Val Gly Thr Ser Ile Val Arg Glu Asn
    115                 120                 125

His Arg Gly Ile Met Ile Thr Ala Leu Ala Ile Ser Tyr Val Ile Ala
130                 135                 140

Glu Gly Val Gly Pro Phe Ile Gly Gly Ala Phe Asn Glu His Leu Ser
145                 150                 155                 160

Trp Arg Trp Cys Phe Tyr Ile Asn Leu Pro Ile Gly Ala Phe Ala Phe
                165                 170                 175

```
Ile Ile Leu Ala Phe Cys Asn Thr Ser Gly Glu Pro His Gln Lys Met
            180                 185                 190

Trp Leu Pro Ser Lys Ile Lys Lys Ile Met Asn Tyr Asp Tyr Gly Glu
        195                 200                 205

Leu Leu Lys Ala Ser Phe Trp Lys Asn Thr Phe Glu Val Leu Val Phe
    210                 215                 220

Lys Leu Asp Met Val Gly Ile Ile Leu Ser Ser Ala Gly Phe Thr Leu
225                 230                 235                 240

Leu Met Leu Gly Leu Ser Phe Gly Gly Asn Asn Phe Pro Trp Asn Ser
            245                 250                 255

Gly Ile Ile Ile Cys Phe Phe Thr Val Gly Pro Ile Leu Leu Leu
        260                 265                 270

Phe Cys Ala Tyr Asp Phe His Phe Leu Ser Leu Ser Gly Leu His Tyr
    275                 280                 285

Asp Asn Lys Arg Ile Lys Pro Leu Leu Thr Trp Asn Ile Ala Ser Asn
290                 295                 300

Cys Gly Ile Phe Thr Ser Ser Ile Thr Gly Phe Leu Ser Cys Phe Ala
305                 310                 315                 320

Tyr Glu Leu Gln Ser Ala Tyr Leu Val Gln Leu Tyr Gln Leu Val Phe
            325                 330                 335

Lys Lys Lys Pro Thr Leu Ala Ser Ile His Leu Trp Glu Leu Ser Ile
        340                 345                 350

Pro Ala Met Ile Ala Thr Met Ala Ile Ala Tyr Leu Asn Ser Lys Tyr
    355                 360                 365

Gly Ile Ile Lys Pro Ala Ile Val Phe Gly Val Leu Cys Gly Ile Val
370                 375                 380

Gly Ser Gly Leu Phe Thr Leu Ile Asn Gly Glu Leu Ser Gln Ser Ile
385                 390                 395                 400

Gly Tyr Ser Ile Leu Pro Gly Ile Ala Phe Gly Ser Ile Phe Gln Ala
            405                 410                 415

Thr Leu Leu Ser Ser Gln Val Gln Ile Thr Ser Asp Asp Pro Asp Phe
        420                 425                 430

Gln Asn Lys Phe Ile Glu Val Thr Ala Phe Asn Ser Phe Ala Lys Ser
    435                 440                 445

Leu Gly Phe Ala Phe Gly Gly Asn Met Gly Ala Met Ile Phe Thr Ala
450                 455                 460

Ser Leu Lys Asn Gln Met Arg Ser Ser Gln Leu Asn Ile Pro Gln Phe
465                 470                 475                 480

Thr Ser Val Glu Thr Leu Leu Ala Tyr Ser Thr Glu His Tyr Asp Gly
            485                 490                 495

Pro Gln Ser Ser Leu Ser Lys Phe Ile Asn Thr Ala Ile His Asp Val
        500                 505                 510

Phe Tyr Cys Ala Leu Gly Cys Tyr Ala Leu Ser Phe Phe Gly Ile
    515                 520                 525

Phe Thr Ser Ser Lys Lys Thr Thr Ile Ser Ala Lys Lys Gln Gln
530                 535                 540

<210> SEQ ID NO 22
<211> LENGTH: 310
<212> TYPE: PRT
<213> ORGANISM: Saccharomyces cerevisiae

<400> SEQUENCE: 22

Met Ile Ser Glu Lys Ala Ala Thr Ala Leu Ala Thr Ile Ala Thr Val
1               5                   10                  15
```

Cys Trp Cys Val Gln Leu Ile Pro Gln Ile Ile Tyr Asn Trp Lys Lys
                20                  25                  30

Lys Asp Cys Thr Gly Leu Pro Pro Leu Met Met Phe Leu Trp Val Val
            35                  40                  45

Ser Gly Ile Pro Phe Ala Ile Tyr Phe Cys Val Ser Lys Gly Asn Val
    50                  55                  60

Ile Leu Gln Val Gln Pro His Leu Phe Met Phe Cys Ser Ile Ser
65                  70                  75                  80

Phe Val Gln Ser Cys Tyr Tyr Pro Pro Ile Ser Met Ala Arg Ser Lys
                85                  90                  95

Ile Val Met Ile Val Ala Ala Ile Ala Ala Asp Val Gly Met Glu
            100                 105                 110

Val Gly Phe Ile Leu Trp Leu Arg Pro Leu Tyr Glu Lys Gly Val Lys
        115                 120                 125

Trp Pro Asp Leu Ile Phe Gly Ile Ser Ala Ser Val Leu Leu Ala Val
130                 135                 140

Gly Leu Leu Pro Pro Tyr Phe Glu Leu Ala Lys Arg Lys Gly Arg Val
145                 150                 155                 160

Ile Gly Ile Asn Phe Ala Phe Leu Phe Ile Asp Ser Leu Gly Ala Trp
                165                 170                 175

Leu Ser Ile Ile Ser Val Ile Leu Gly Asn Met Asp Ile Met Gly Ile
            180                 185                 190

Ile Leu Tyr Ser Ile Val Ala Gly Met Glu Leu Gly Ile Phe Ala Ser
        195                 200                 205

His Phe Ile Trp Trp Cys Arg Phe Arg Phe Leu Ala Lys Gly Asn Thr
210                 215                 220

Phe Asp Glu Glu Ser Gly Gln Ala Gln Lys Glu Glu Pro Asp Glu Lys
225                 230                 235                 240

Ile Glu Gln Asp Ile Ser Lys Ser Asp Arg Asn Val Thr Asn Tyr Asn
                245                 250                 255

Leu Asp Asn Cys Ser Ile Pro Asp Asp Ala Ser Ser Phe Ala Asp Asp
            260                 265                 270

Phe Asn Ile Tyr Asp Ser Thr Asp Gly Gly Thr Leu Ser Arg Ala Gln
        275                 280                 285

Thr Leu His Ala Val His Gly Val Val Val Arg Thr Asp Pro Asp Arg
290                 295                 300

Tyr Ser Arg Leu Ser Val
305                 310

<210> SEQ ID NO 23
<211> LENGTH: 56
<212> TYPE: PRT
<213> ORGANISM: Acinetobacter baumannii

<400> SEQUENCE: 23

Met Ser Tyr Leu Tyr Leu Ala Ile Ala Ile Ala Cys Glu Val Ile Ala
1               5                   10                  15

Thr Ser Ala Leu Lys Ala Ser Gln Gly Phe Thr Val Pro Ile Pro Ser
            20                  25                  30

Ile Ile Thr Val Val Gly Tyr Ala Val Ala Phe Tyr Leu Leu Ser Leu
        35                  40                  45

Thr Leu Lys Thr Ile Pro Ile Gly
50                  55

<210> SEQ ID NO 24
<211> LENGTH: 37
<212> TYPE: PRT
<213> ORGANISM: Acinetobacter baumannii

<400> SEQUENCE: 24

Met Lys Met Ser Glu Gly Phe Thr Arg Leu Thr Pro Ser Ile Ile Thr
1               5                   10                  15

Val Val Phe Met Ile Leu Ser Val Val Leu Leu Ser Ile Ser Met Lys
            20                  25                  30

Thr Leu Pro Leu Gly
        35

<210> SEQ ID NO 25
<211> LENGTH: 57
<212> TYPE: PRT
<213> ORGANISM: Escherichia coli

<400> SEQUENCE: 25

Met Asn Pro Tyr Ile Tyr Leu Gly Gly Ala Ile Leu Ala Glu Val Ile
1               5                   10                  15

Gly Thr Thr Leu Met Lys Phe Ser Glu Gly Phe Thr Arg Leu Trp Pro
            20                  25                  30

Ser Val Gly Thr Ile Ile Cys Tyr Cys Ala Ser Phe Trp Leu Leu Ala
        35                  40                  45

Gln Thr Leu Ala Tyr Ile Pro Thr Gly
    50                  55

<210> SEQ ID NO 26
<211> LENGTH: 57
<212> TYPE: PRT
<213> ORGANISM: Serratia marcescens

<400> SEQUENCE: 26

Met Ser Ala Phe Met Tyr Leu Thr Met Ala Ile Val Ala Glu Val Ile
1               5                   10                  15

Ala Thr Thr Met Leu Lys Ala Ser Glu Gly Phe Thr Arg Leu Trp Pro
            20                  25                  30

Ser Leu Leu Val Val Leu Gly Tyr Gly Val Ala Phe Trp Gly Leu Ser
        35                  40                  45

Met Val Val Lys Ser Met Pro Leu Gly
    50                  55

<210> SEQ ID NO 27
<211> LENGTH: 57
<212> TYPE: PRT
<213> ORGANISM: Klebsiella aerogenes

<400> SEQUENCE: 27

Met Lys Gly Trp Leu Phe Leu Val Ile Ala Ile Val Gly Glu Val Ile
1               5                   10                  15

Ala Thr Ser Ala Leu Lys Ser Ser Glu Gly Phe Thr Lys Leu Ala Pro
            20                  25                  30

Ser Ala Val Val Ile Ile Gly Tyr Gly Ile Ala Phe Tyr Phe Leu Ser
        35                  40                  45

Leu Val Ile Lys Ser Ile Pro Val Gly
    50                  55

<210> SEQ ID NO 28
<211> LENGTH: 57

```
<212> TYPE: PRT
<213> ORGANISM: Enterobacter aerogenes

<400> SEQUENCE: 28

Met Lys Asn Trp Ile Phe Leu Ala Val Ser Ile Phe Gly Glu Val Ile
1               5                   10                  15

Ala Thr Ser Ala Leu Lys Ser Ser His Gly Phe Thr Arg Leu Val Pro
            20                  25                  30

Ser Val Val Val Ala Gly Tyr Gly Leu Ala Phe Tyr Phe Leu Ser
        35                  40                  45

Leu Ala Leu Lys Ser Ile Pro Val Gly
    50                  55

<210> SEQ ID NO 29
<211> LENGTH: 56
<212> TYPE: PRT
<213> ORGANISM: Staphylococcus aureus

<400> SEQUENCE: 29

Met Pro Tyr Ile Tyr Leu Ile Ile Ala Ile Ser Thr Glu Val Ile Gly
1               5                   10                  15

Ser Ala Phe Leu Lys Ser Ser Glu Gly Phe Ser Lys Phe Ile Pro Ser
            20                  25                  30

Leu Gly Thr Ile Ile Ser Phe Gly Ile Cys Phe Tyr Phe Leu Ser Lys
        35                  40                  45

Thr Met Gln His Leu Pro Leu Asn
    50                  55

<210> SEQ ID NO 30
<211> LENGTH: 56
<212> TYPE: PRT
<213> ORGANISM: Staphylococcus saprophyticus

<400> SEQUENCE: 30

Met Pro Tyr Leu Tyr Leu Leu Leu Ser Ile Val Ser Glu Val Ile Gly
1               5                   10                  15

Ser Ala Phe Leu Lys Ser Ser Asp Gly Phe Ser Lys Leu Tyr Pro Thr
            20                  25                  30

Ile Thr Thr Ile Ile Ser Phe Leu Ile Cys Phe Tyr Phe Leu Ser Lys
        35                  40                  45

Thr Met Gln His Leu Pro Leu Asn
    50                  55

<210> SEQ ID NO 31
<211> LENGTH: 56
<212> TYPE: PRT
<213> ORGANISM: Staphylococcus sp. ST94

<400> SEQUENCE: 31

Met His Tyr Leu Tyr Leu Phe Ile Ser Ile Ala Thr Glu Ile Ile Gly
1               5                   10                  15

Thr Ser Phe Leu Lys Thr Ser Glu Gly Phe Thr Lys Leu Trp Pro Thr
            20                  25                  30

Leu Gly Thr Leu Leu Ser Phe Gly Ile Cys Phe Tyr Phe Leu Ser Leu
        35                  40                  45

Thr Ile Lys Phe Leu Pro Leu Asn
    50                  55

<210> SEQ ID NO 32
```

```
<211> LENGTH: 58
<212> TYPE: PRT
<213> ORGANISM: Bacillus subtilis

<400> SEQUENCE: 32

Met Leu Ile Gly Tyr Ile Phe Leu Thr Ile Ala Ile Cys Ser Glu Ser
1               5                   10                  15

Ile Gly Ala Ala Met Leu Lys Val Ser Asp Gly Phe Lys Lys Trp Lys
            20                  25                  30

Pro Ser Ala Leu Val Val Ile Gly Tyr Ser Leu Ala Phe Tyr Met Leu
        35                  40                  45

Ser Leu Thr Leu Asn His Ile Pro Leu Ser
    50                  55

<210> SEQ ID NO 33
<211> LENGTH: 57
<212> TYPE: PRT
<213> ORGANISM: Bacillus subtilis

<400> SEQUENCE: 33

Met Arg Gly Leu Leu Tyr Leu Ala Leu Ala Ile Val Ser Glu Val Phe
1               5                   10                  15

Gly Ser Thr Met Leu Lys Leu Ser Glu Gly Phe Thr Gln Ala Trp Pro
            20                  25                  30

Ile Ala Gly Val Ile Val Gly Phe Leu Ser Ala Phe Thr Phe Leu Ser
        35                  40                  45

Phe Ser Leu Thr Lys Ile Asp Leu Ser
    50                  55

<210> SEQ ID NO 34
<211> LENGTH: 57
<212> TYPE: PRT
<213> ORGANISM: Mycobacterium tuberculosis

<400> SEQUENCE: 34

Met Ile Tyr Leu Tyr Leu Leu Cys Ala Ile Phe Ala Glu Val Val Ala
1               5                   10                  15

Thr Ser Leu Leu Lys Ser Thr Glu Gly Phe Thr Arg Leu Trp Pro Thr
            20                  25                  30

Val Gly Cys Leu Val Gly Tyr Gly Ile Ala Phe Ala Leu Leu Ala Leu
        35                  40                  45

Ser Ile Ser His Gly Met Gln Thr Asp
    50                  55

<210> SEQ ID NO 35
<211> LENGTH: 53
<212> TYPE: PRT
<213> ORGANISM: Bacillus subtilis

<400> SEQUENCE: 35

Met Arg Trp Gly Ser Val Ile Leu Ala Ala Leu Phe Glu Ile Gly Trp
1               5                   10                  15

Val Met Gly Leu Lys His Ala Asp Ser Ala Leu Glu Trp Ile Cys Thr
            20                  25                  30

Ala Ala Ala Val Val Met Ser Phe Tyr Ile Leu Val Lys Ala Gly Glu
        35                  40                  45

Lys Leu Pro Val Gly
    50
```

```
<210> SEQ ID NO 36
<211> LENGTH: 57
<212> TYPE: PRT
<213> ORGANISM: Pseudomonas aeruginosa

<400> SEQUENCE: 36

Met Ala Trp Ile Tyr Leu Ile Leu Ala Gly Leu Phe Glu Ile Gly Trp
1               5                   10                  15

Pro Val Gly Leu Lys Met Ala Gln Val Pro Glu Thr Arg Trp Ser Gly
            20                  25                  30

Val Gly Ile Ala Val Ala Phe Met Ala Val Ser Gly Phe Leu Leu Trp
        35                  40                  45

Leu Ala Gln Arg His Ile Pro Ile Gly
    50                  55

<210> SEQ ID NO 37
<211> LENGTH: 56
<212> TYPE: PRT
<213> ORGANISM: Escherichia coli

<400> SEQUENCE: 37

Met Ser Trp Ile Val Leu Leu Ile Ala Gly Leu Leu Glu Val Val Trp
1               5                   10                  15

Ala Ile Gly Leu Lys Tyr Thr His Gly Phe Thr Arg Leu Thr Pro Ser
            20                  25                  30

Ile Ile Thr Ile Ala Ala Met Ile Val Ser Ile Ala Met Leu Ser Trp
        35                  40                  45

Ala Met Arg Thr Leu Pro Val Gly
    50                  55

<210> SEQ ID NO 38
<211> LENGTH: 56
<212> TYPE: PRT
<213> ORGANISM: Bacillus subtilis

<400> SEQUENCE: 38

Met Glu Trp Ile Cys Leu Ile Ala Ala Gly Ile Leu Glu Met Leu Gly
1               5                   10                  15

Val Thr Met Met Asn Gln Phe His Lys Asp Lys Arg Val Arg Trp Ile
            20                  25                  30

Phe Leu Leu Ile Ile Gly Phe Ala Ala Ser Phe Phe Leu Leu Ser Leu
        35                  40                  45

Ala Met Glu Thr Leu Pro Met Gly
    50                  55
```

ENGINEERED MICROORGANISMS HAVING RESISTANCE TO IONIC LIQUIDS

CROSS-REFERENCE TO RELATED APPLICATION

This application claims priority to U.S. Provisional Patent Application Ser. No. 62/001,014, filed on May 20, 2014, which is hereby incorporated by reference.

STATEMENT OF GOVERNMENTAL SUPPORT

This invention was made with government support under Contract No. DE-AC02-05CH11231 awarded by the United States Department of Energy and Award No. EEC-0540879 awarded by the National Science Foundation. The government has certain rights in the invention.

FIELD OF THE INVENTION

This invention relates generally to microbial resistance to ionic liquids.

BACKGROUND OF THE INVENTION

Biomass feedstock pretreatment with ionic liquids (ILs) reduces recalcitrance of lignocellulose to degradation. However, ILs are often toxic to microorganisms used subsequently for saccharification and fermentation and the low levels of IL that can remain after pretreatment inhibit the growth of organism used in saccharification and/or fermentation reactions. There is therefore a need to improve IL tolerance of such organisms. This invention addresses this need.

SUMMARY OF THE INVENTION

In one aspect, this invention relates to a method of increasing tolerance of a microorganism, e.g., *Escherichia coli*, to ILs. The method comprises engineering the microorganism to express a gene encoding a yeast Major Facilitator Superfamily (MFS) protein, or a *Salmonella* MFS SmvA Pump or SmvR Regulator. The invention further provides recombinant microorganisms engineered to express a yeast MFS protein, or *Salmonella* MFS SmvA Pump or SmvR Regulator, and methods employing such microorganisms to process biomass.

In one aspect, the invention provides a recombinant microorganism having resistance to ionic liquids, e.g., an ionic liquid where the anion is Cl⁻ or acetate, wherein the microorganism comprises a heterologous gene encoding a yeast MFS, or *Salmonella* MFS SmvA Pump or SmvR Regulator, polypeptide wherein the yeast MFS polypeptide has at least 70% identity, or at least 75%, 80%, or 85% identity, to SEQ ID NO:21, or SEQ ID NOs:1 or 2. In some embodiments, the yeast MFS, or *Salmonella* MFS SmvA Pump or SmvR Regulator, polypeptide has at least 90% identity, or at least 95% identity, or at least 99% identity, to SEQ ID NO:21, or SEQ ID NOs: 1 or 2. In some embodiments, the polypeptide comprises SEQ ID NO:21, or SEQ ID NOs:1 or 2. In some embodiments, the heterologous gene is operably linked to a tet repressor sequence. In some embodiments, the microorganism is also genetically modified to express a tet repressor protein that binds to the tet repressor sequence. In some embodiments, the microorganism is a yeast or filamentous fungi. In some embodiments, the heterologous gene encoding the yeast MFS, or *Salmonella* MFS SmvA Pump or SmvR Regulator, polypeptide is integrated into the genome of the microorganism. In some embodiments, the heterologous gene encoding the yeast MFS, or *Salmonella* MFS SmvA Pump or SmvR Regulator, polypeptide is present on an extrachromosomal autonomously replicating sequence present in the microorganism.

In a further aspect, the invention provides a method of modifying a microorganism to have resistance to ionic liquids, e.g., ionic liquids where the anion is Cl⁻ or acetate, the method comprising introducing an expression cassette into the microorganism, wherein the expression cassette comprises a gene encoding a yeast MFS, or *Salmonella* MFS SmvA Pump or SmvR Regulator, polypeptide that has at least 70% identity, or at least 75%, 80%, or 85% identity, to SEQ ID NO:21, or SEQ ID NOs:1 or 2. In some embodiments, the yeast MFS, or *Salmonella* MFS SmvA Pump or SmvR Regulator, polypeptide has at least 90% identity, or at least 95% identity, or at least 99% identity, to SEQ ID NO:21, or SEQ ID NOs:1 or 2. In other embodiments the polypeptide comprises SEQ ID NO:21, or SEQ ID NOs:1 or 2. In some embodiments, the heterologous gene is operably linked to a tet repressor sequence. In some embodiments, the method further comprises engineering the microorganism to express a tet repressor that binds to the tet repressor sequence. In some embodiments, the method comprises engineering bacteria, such as *Escherichia coli*. In other embodiments, the method comprises engineering a yeast or filamentous fungi. In some embodiments, the method comprises integrating the heterologous gene encoding the yeast MFS, or *Salmonella* MFS SmvA Pump or SmvR Regulator, polypeptide into the genome of the microorganism.

In a further aspect, the invention provides a composition comprising a microorganism of the invention comprising a heterologous yeast MFS, or *Salmonella* MFS SmvA Pump or SmvR Regulator, gene that is capable of expressing yeast MFS, or bacterial MFS. In some embodiments, the composition is a reaction mixture that comprises an ionic liquid and the microorganism of the invention. In some embodiments, the reaction mixture further comprises biomass.

In an additional aspect, the invention provides a method of increasing the yield of soluble sugar from a biomass, the method comprising incubating biomass pretreated with a microorganism genetically modified to comprise a heterologous yeast MFS, or *Salmonella* MFS SmvA Pump or SmvR Regulator, gene in an enzymatic hydrolysis reaction. The invention additionally provides a method of increasing the yield from a reaction in which soluble sugars are a source of carbon, e.g., a fermentation reaction that produces a biofuel, such as an alcohol, the method comprising incubating biomass pretreated with ionic liquid with a microorganism of the invention in a reaction.

In one aspect, this invention relates to a method of increasing tolerance of a microorganism, e.g., *Escherichia coli*, to ILs. The method comprises engineering the microorganism to express a gene encoding a Small Multidrug Resistance Family (SMR) protein. The invention further provides recombinant microorganisms engineered to express a SMR protein and methods employing such microorganisms to process biomass.

In one aspect, the invention provides a recombinant microorganism having resistance to ionic liquids, e.g., an ionic liquid where the anion is Cl⁻ or acetate, wherein the microorganism comprises a heterologous gene encoding a SMR polypeptide, wherein the SMR polypeptide has at least 70% identity, or at least 75%, 80%, or 85% identity, to one amino acid sequence of the group consisting of SEQ ID NOs:3-20. In some embodiments, the SMR polypeptide has at least 90% identity, or at least 95% identity, or at least 99% identity, to one amino acid sequence of the group consisting of SEQ ID NOs: 3-20. In some embodiments, the polypeptide comprises one amino acid sequence of the group consisting of SEQ ID NOs: 3-20. In some embodiments, the heterologous gene is operably linked to a tet repressor sequence. In some embodiments, the microorganism is also genetically modified to express a tet repressor protein that binds to the tet repressor sequence. In some embodiments, the microorganism is a yeast or filamentous fungi. In some embodiments, the heterologous gene encoding the SMR polypeptide is integrated into the genome of the microorganism. In some embodiments, the heterologous gene encoding the SMR polypeptide is present on an extrachromosomal autonomously replicating sequence present in the microorganism.

In a further aspect, the invention provides a method of modifying a microorganism to have resistance to ionic liquids, e.g., ionic liquids where the anion is Cl⁻ or acetate, the method comprising introducing an expression cassette into the microorganism, wherein the expression cassette comprises a gene encoding a SMR polypeptide that has at least 70% identity, or at least 75%, 80%, or 85% identity, to one amino acid sequence of the group consisting of SEQ ID NOs: 3-20. In some embodiments, the SMR polypeptide has at least 90% identity, or at least 95% identity, or at least 99% identity, to one amino acid sequence selected from the group consisting of SEQ ID NOs: 3-20. In other embodiments the polypeptide comprises one amino acid sequence selected from the group consisting of SEQ ID NOs: 3-20. In some embodiments, the heterologous gene is operably linked to a tet repressor sequence. In some embodiments, the method further comprises engineering the microorganism to express a tet repressor that binds to the tet repressor sequence. In some embodiments, the method comprises engineering bacteria, such as *Escherichia coli*. In other embodiments, the method comprises engineering a yeast or filamentous fungi. In some embodiments, the method comprises integrating the heterologous gene encoding the SMR polypeptide into the genome of the microorganism.

In a further aspect, the invention provides a composition comprising a microorganism of the invention comprising a heterologous SMR gene that is capable of expressing SMR. In some embodiments, the composition is a reaction mixture that comprises an ionic liquid and the microorganism of the invention. In some embodiments, the reaction mixture further comprises biomass.

In an additional aspect, the invention provides a method of increasing the yield of soluble sugar from a biomass, the method comprising incubating biomass pretreated with a microorganism genetically modified to comprise a heterologous SMR gene in an enzymatic hydrolysis reaction. The invention additionally provides a method of increasing the yield from a reaction in which soluble sugars are a source of carbon, e.g., a fermentation reaction that produces a biofuel, such as an alcohol, the method comprising incubating biomass pretreated with ionic liquid with a microorganism of the invention in a reaction.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

Figures 1, 2:
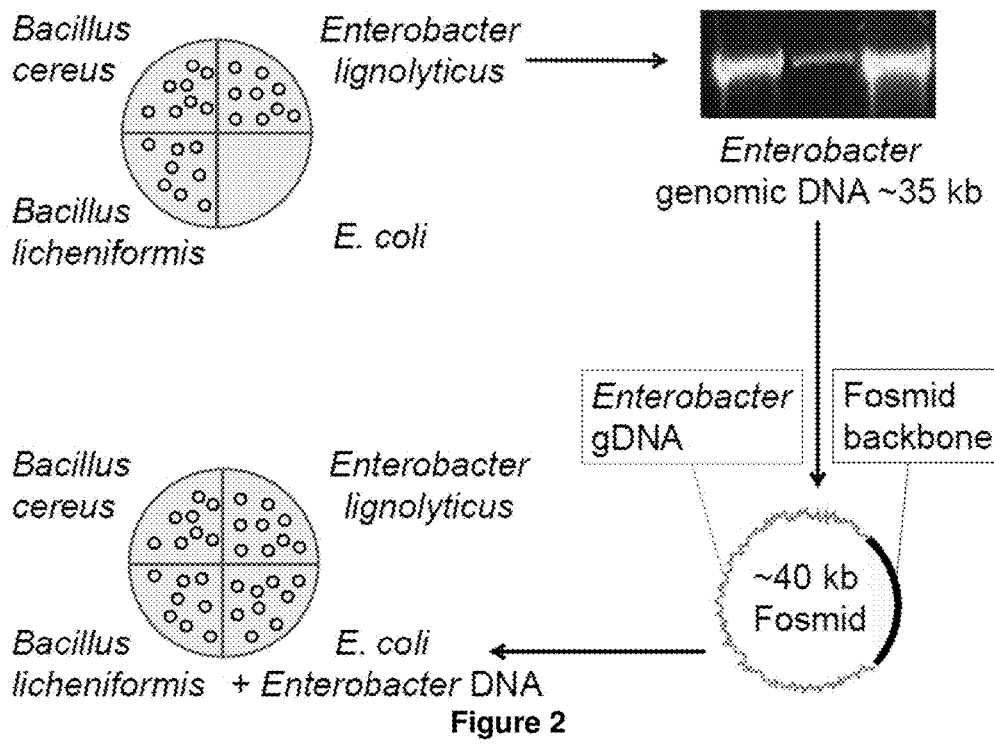
FIG. 1 shows the multiple sequence alignment of the first about fifty-six amino acids of SMR efflux proteins. Multiple sequence alignment was generated using ClustalW. Secondary structure elements indicated on top correspond to those observed in the *E. coli* EmrE protein (Protein Data Bank identification no. 3b5d). The first two probable transmembrane segments (TMS) are indicated with horizontal lines above the alignments. Asterisks indicate fully conserved residues, colons indicate strongly similar residues, and dots indicate weakly similar residues. Dashes represent gaps. Essential residues (as shown in EmrE [Schuldiner, S. 2007. When biochemistry meets structural biology: the cautionary tale of EmrE. *Trends Biochem. Sci.* 32:252-258]) are highlighted in black. Conserved residues are highlighted in gray. The identities (ID) and similarities (SM) of AbeS with the corresponding SMR transporter are shown in their respective column. Sequences were obtained from the GenBank database by the use of the following (protein) accession numbers: AbeS, *A. baumannii* AC0037 (FJ843079) (SEQ ID NO:23); *A. baumannii* AYE (YP_001713109.1) (SEQ ID NO:23); AB0057 (YP_002319996.1) (SEQ ID NO:23); AB307-0294 (YP_002325052.1) (SEQ ID NO:23); ATCC 17978 (YP_001085323.1) (SEQ ID NO:24); EmrE, *E. coli* (P23895.1) (SEQ ID NO:25); SsmE, *S. marcescens* (BAF80121.1) (SEQ ID NO:26); QacE, *K. aerogenes* (P0AGD0.1) (SEQ ID NO:27); QacEdelta1, *Klebsiella pneumoniae* (ABF48386.1) (SEQ ID NO:27); QacF, *Enterobacter aerogenes* (Q9X2N9.1) (SEQ ID NO:28); QacC, *Staphylococcus aureus* (AAM94143.1) (SEQ ID NO:29); QacH, *Staphylococcus saprophyticus* (O87868.1) (SEQ ID NO:30); QacG, *Staphylococcus* sp. strain ST94 (O87866.1) (SEQ ID NO:31); EbrA, *Bacillus subtilis* (O31792.1) (SEQ ID NO:32); EbrB, *B. subtilis* (O31791.1) (SEQ ID NO:33); Mmr, *Mycobacterium tuberculosis* (P95094) (SEQ ID NO:34); YkkC, *B. subtilis* (Q65KV1.1) (SEQ ID NO:35); Smr-2, *Pseudomonas aeruginosa* (CAH04647.1) (SEQ ID NO:36); SugE, *E. coli* (AAQ16658.1) (SEQ ID NO:37); and YkkD, *B. subtilis* (Q65KV0.1) (SEQ ID NO:38).
FIG. 2 shows screening for IL tolerance in *E. coli*.
Figure 3:
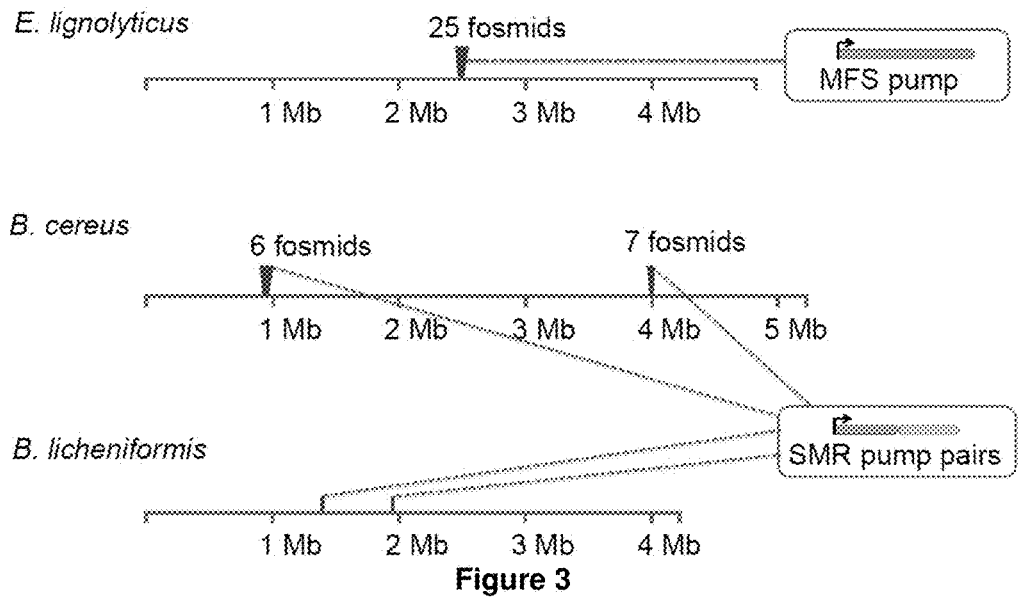
FIG. 3 shows identifying bacterial IL tolerance genes.
Figure 4:
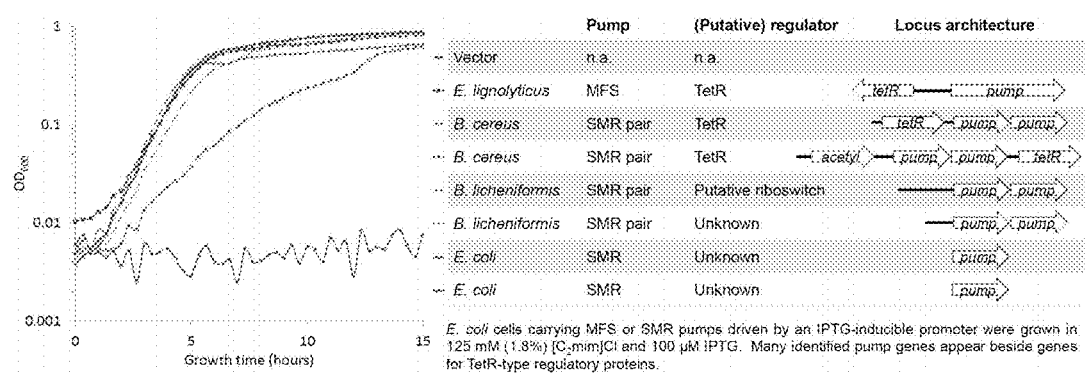
FIG. 4 shows pump expression rescues *E. coli* growth in IL.
Figure 5:
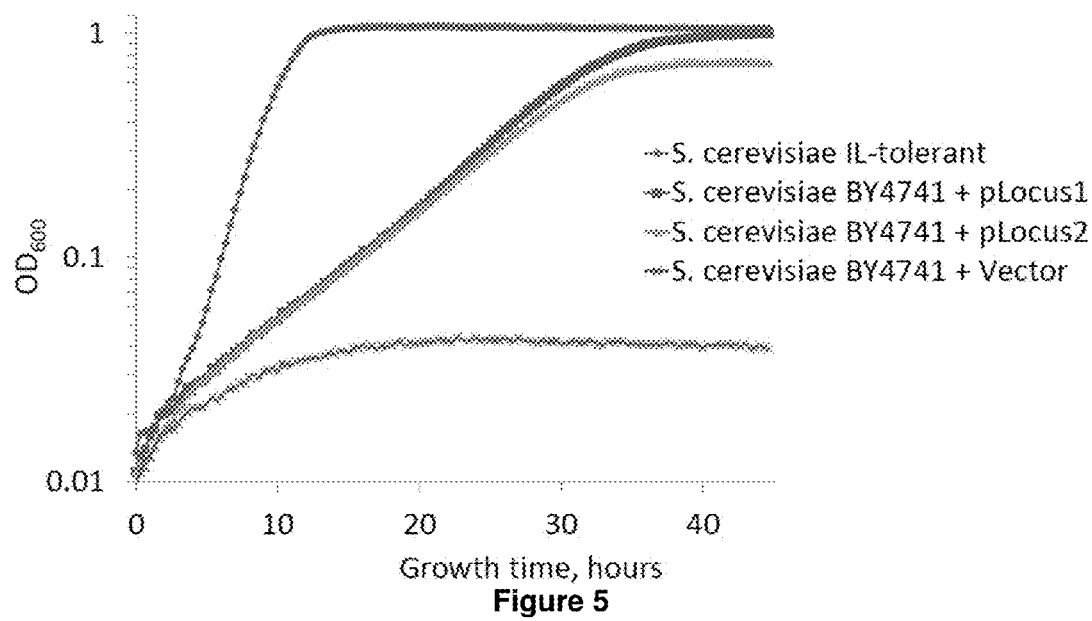
FIG. 5 shows identifying yeast IL tolerance genes.
Figure 6:
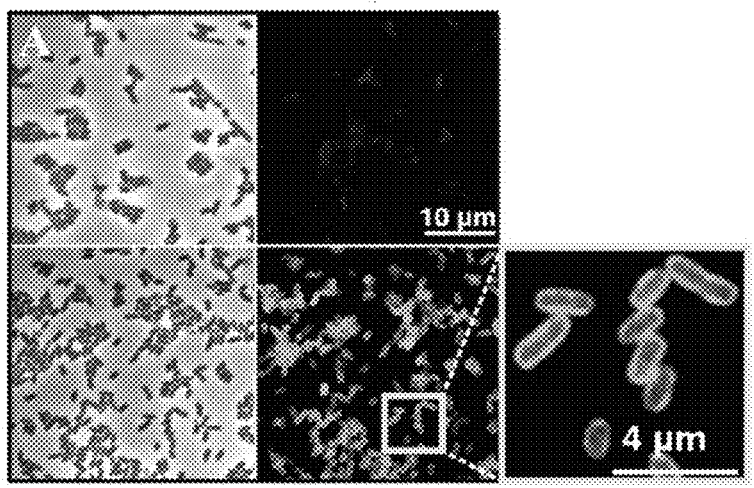
FIG. 6 shows the IL-inducible repressor EilR regulates efflux pump expression in *E. coli*.
Figure 6:
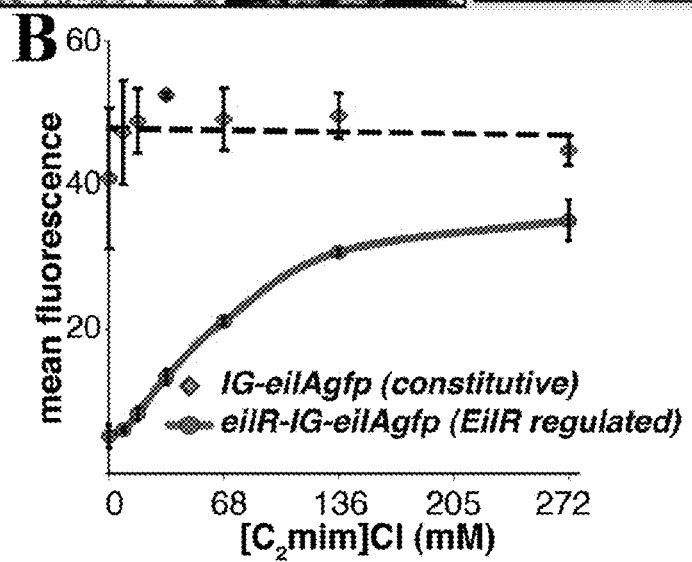
Figure 6:
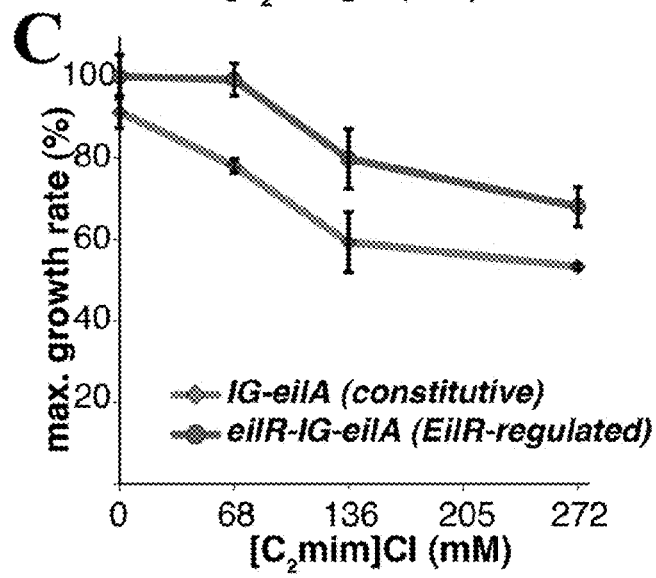

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a molecule" includes a plurality of such molecules, and so forth.

The term "about" indicates a value including 10% more than the stated value and 10% less than the stated value. When used to describe a number of nucleotides, it also includes a number of nucleotides one more and/or one fewer than the stated number.

These and other objects, advantages, and features of the invention will become apparent to those persons skilled in the art upon reading the details of the invention as more fully described below.

Definitions

As used herein, the term "Small Multidrug Resistance Family protein" or "SMR protein" are used interchangeably to refer to a membrane protein that functions as a transporter of small molecules, or a regulator thereof. The term encompasses variants and interspecies homologs of the specific polypeptides described herein. A nucleic acid that encodes a SMR protein refers to a gene, cDNA, pre-mRNA, mRNA, and the like, including nucleic acids encoding variants and interspecies homologs of the particular amino acid sequences described herein. Thus, in some embodiments, SMR gene encodes a polypeptide having an amino acid sequence that has at least 40% amino acid sequence identity, or at least 45%, 50%, 55%, 60%, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 300 or more amino acids, or over the length of the entire polypeptide, to an amino acid sequence selected from the group consisting of SEQ ID NOs:3-20. Any one amino acid sequence selected from the group consisting of SEQ ID NOs: 3-20 provides an illustrative amino acid sequence of a SMR proteins suitable for use in the invention.

As used herein, the term "Major Facilitator Superfamily protein" or "MFS protein" are used interchangeably to refer to a membrane protein that functions as a transporter of small molecules, or a regulator thereof. The term encompasses variants and interspecies homologs of the specific polypeptides described herein. A nucleic acid that encodes a MFS protein refers to a gene, cDNA, pre-mRNA, mRNA, and the like, including nucleic acids encoding variants and interspecies homologs of the particular amino acid sequences described herein. Thus, in some embodiments, MFS gene encodes a polypeptide having an amino acid sequence that has at least 40% amino acid sequence identity, or at least 45%, 50%, 55%, 60%, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 300 or more amino acids, or over the length of the entire polypeptide, to an amino acid sequence selected from the group consisting of SEQ ID NOs:1, 2, and 21. Any one amino acid sequence selected from the group consisting of SEQ ID NOs:1, 2, and 21 provides an illustrative amino acid sequence of a MFS proteins suitable for use in the invention.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 40%, 45%, or 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below. For example, a polynucleotide encoding a SMR polypeptide may have a sequence that is at least 50%, 55%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NOs: 3-20.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity)

and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are illustrative conservative substitutions for one another. 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see, e.g., Creighton, *Proteins* (1984)).

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular species, but also encompasses a promoter from a corresponding gene in other species.

A "constitutive promoter" in the context of this invention refers to a promoter that is capable of initiating transcription under most conditions in a cell, e.g., in the absence of an inducing molecule, whereas an "inducible promoter" initiates transcription in the presence of an inducer molecule.

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety)

"Recombinant nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence will have two or more sequences from unrelated genes arranged to make a new functional nucleic acid.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a MFS or SMR protein operably linked to a promoter, e.g., its native promoter, where the expression cassette is introduced into a heterologous microorganism. In some embodiments, an expression cassette comprises a polynucleotide sequence encoding a MFS or SMR protein that is targeted to a position in the genome of a microorganism such that expression of the polynucleotide sequence is driven by a promoter that is present in the microorganism.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used herein and in the appended claims, the singular "a", "an" and "the" include the plural reference unless the context clearly dictates otherwise. Thus, for example, reference to a "host cell" includes a plurality of such host cells.

Introduction

Ionic liquids are used to pretreat biomass to improve the yield of soluble sugars from downstream reactions such as enzymatic hydrolysis. The invention provides methods of genetically modifying microorganisms, e.g., bacteria such as *E. coli* or yeast, to have resistance to ionic liquids.

A microorganism is typically genetically modified to express a heterologous MFS or SMR protein by introducing an expression cassette that comprises a polynucleotide encoding an MFS or SMR protein operably linked to a promoter into a microbial host cell. In some embodiments, the promoter is a constitutive promoter. In some embodiments, the promoter comprises a repressor binding site for a repressor, e.g., a tet repressor, that dissociates from the binding site when ionic liquids are present in the media in which the host cell is growing.

A microorganism modified as described herein is used in reactions that employ ionic liquids, for example, reactions comprising biomass pretreated with ionic liquids. A genetically modified microorganism as described herein provides for increased yields of soluble sugars from IL-pretreated biomass in comparison to a microorganism that has not been genetically modified to express a heterologous MFS or SMR protein. Further, a microorganism modified to express MFS or SMR can also provide a growth advantage over a contaminating microorganism that may be present in a reaction, such as a fermentation reaction.

Genetically modified microorganisms engineered to express MFS or SMR can also be used for any other reactions in which it is desirable to use a microorganism that is tolerant to ionic liquids. For example, such an organism can be used in pharmaceutical reactions or other reactions where ionic liquids are used as replacement for organic solvents.

MFS and SMR Nucleic Acid Sequences

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009, supplements through 2012).

MFS nucleic acid and polypeptide sequences suitable for use in the invention include MFS nucleic acid sequences that encode a MFS polypeptide as illustrated in SEQ ID NO:1, 2, and 21, or a substantially identical variants. Such a variant typically has at least 60%, often at least 70%, or at least 75%, 80%, 85%, or 90% identity to SEQ ID NO:1, 2, and 21.

SMR nucleic acid and polypeptide sequences suitable for use in the invention include SMR nucleic acid sequences that encode a SMR polypeptide as illustrated in SEQ ID NO:3-20, or a substantially identical variants. Such a variant typically has at least 60%, often at least 70%, or at least 75%, 80%, 85%, or 90% identity to SEQ ID NO:3-20.

Various regions of MFS protein are defined. The typical MFS polypeptide has 14 transmembrane domains. One of skill can obtain or identify a MFS variant for use in the invention by using the sequence alignments to identify residues within the conserved sequences that would be expected to retain function as well as residues outside of the conserved regions that would be tolerant to substitution. In some embodiments, the MFS polypeptide comprises one or more, or all, of the 14 transmembrane domains.

Various regions of SMR protein are defined. For example, the typical SMR polypeptide has 4 transmembrane domains. The helical regions of the first two domains are present on amino acids 1-22 and 31-52 for YkkD. An alignment of some of these SMR proteins is shown in FIG. 1. One of skill can obtain or identify a SMR variant for use in the invention by using the sequence alignments to identify residues within the conserved sequences that would be expected to retain function as well as residues outside of the conserved regions that would be tolerant to substitution. In some embodiments, the SMR polypeptide comprises one or more, or all, of the 4 transmembrane domains, and/or one or more of the conserved amino acid residues identified in FIG. 1.

In some embodiments, an MFS or SMR polypeptide may be modified to have a signal sequence. For example, in some embodiments, it may be desirable to employ a signal sequence from the host cell into which the MFS or SMR gene will be introduced.

MFS or SMR activity for conferring resistance to an IL can be assessed using any number of assays. For example, a gene encoding an MFS or SMR protein can be introduced into a microorganism, such as a bacteria, e.g., *E. coli*, and tested for the ability to grow in the presence of an IL. In the present invention, a microorganism that is resistant to an ionic liquid has improved growth in the presence of the ionic liquid when compared to the same microorganism, i.e., the same genetic background, that has not been modified to express an MFS or SMR polypeptide. In typical embodiments, growth is increased by at least 10%, 20%, 30%, 40%, or 50% or more compared the control, unmodified organism. In some embodiments, the amount of ionic liquid employed in testing is in the range of from about 1% to about to about 20% IL, e.g., about 1%, 2%, 3%, 4%, 5%, 6%, 7%, 8%, 9%, 10%, or 15% or 20%, added to the culture medium. In some embodiments, the amount of ionic liquid employed in testing is at least about 0.1% added to the culture medium. In some embodiments, the ionic liquid is [$C_2$mim]Cl. In the context of this invention, a microorganism modified to express a heterologous MFS or SMR polypeptide is generally resistant to at least 2% ionic liquid, and in some embodiments, is resistant to at least 10% or 20% ionic liquid, e.g., is resistant to at least 20% [$C_2$mim]Cl. In some embodiments, a microorganism modified to express a heterologous SMR polypeptide is resistant to at least 0.1% ionic liquid.

Isolation or generation of MFS or SMR polynucleotide sequences can be accomplished by any number of techniques well known in the art. In some embodiments, oligonucleotide probes based on the sequences disclosed herein can be used to identify the desired polynucleotide in a cDNA or genomic DNA library from a desired bacterial species. Probes may be used to hybridize with genomic DNA or cDNA sequences to isolate homologous genes in the same or different bacterial species.

Alternatively, the nucleic acids of interest can be amplified from nucleic acid samples using routine amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying a MFS or SMR gene from bacterial cells such as *Enterobacter* cells, can be generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990).

MFS or SMR nucleic acid sequences for use in the invention includes genes and gene products identified and characterized by techniques such as hybridization and/or sequence analysis using exemplary nucleic acid sequences, e.g., SEQ ID NOs:1 or 4.

MFS- or SMR-encoding nucleic acid sequences may additionally be codon-optimized for expression in a desired host cell. Methods and databases that can be employed are known in the art. For example, preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. See, e.g., See e.g., Henaut and Danchin in "*Escherichia coli* and *Salmonella*," Neidhardt, et al. Eds., ASM Pres, Washington D.C. (1996), pp. 2047-2066; Nucleic Acids Res. 20:2111-2118; Nakamura et al., 2000, Nucl. Acids Res. 28:292.

Preparation of Recombinant Vectors

To use isolated sequences in the above techniques, recombinant DNA vectors suitable for transformation of host cells are prepared. Preparation of recombinant vectors is well known in the art. For example, a DNA sequence encoding a MFS or SMR polypeptide can be combined with transcriptional and other regulatory sequences which will direct the transcription of the sequence from the gene in the intended cells. In some embodiments, an expression vector that comprises an expression cassette that comprises the MFS or SMR gene further comprises a promoter operably linked to the MFS or SMR gene. Such a promoter can be an MFS or SMR promoter from the native MFS or SMR gene or a heterologous promoter. In other embodiments, a promoter and/or other regulatory elements that direct transcription of the MFS or SMR gene are endogenous to the microorganism and an expression cassette comprising the MFS or SMR gene is introduced, e.g., by homologous recombination, such that the heterologous MFS or SMR gene is operably linked to an endogenous promoter and is expression driven by the endogenous promoter.

Expression of the MFS or SMR gene can be controlled by a number of regulatory sequences including promoters, which may be either constitutive or inducible; and, optionally, repressor sequences. Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. In some embodiments, an SMR gene is operably linked to a nucleotide sequence comprising a tet repressor binding site.

Additional examples of regulatory regions that can be used to regulate expression of a MFS or SMR gene under a desired environmental conditions include lactose promoters (Lac repressor protein changes conformation when contacted with lactose, thereby preventing the Lac repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter. (See deBoer et al. (1983) Proc. Natl. Acad. ScL USA, 80:21-25.) As will be appreciated by those of ordinary skill in the art, these and other expression vectors may be used in the present invention, and the invention is not limited in this respect.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from the gene encoding neutral alpha-amylase in *Aspergillus niger* In which the untranslated leader has been replaced by an untranslated leader from the gene encoding triose phosphate isomerase in *Aspergillus nidulans*); and mutant, truncated, and hybrid promoters thereof.

Suitable promoters of use in a yeast host cell include promoters obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

An expression vector may also comprise additional sequences that influence expression of an MFS or SMR gene. Such sequences include enhancer sequences or other sequences such as transcription termination sequences, and the like.

A vector expressing an MFS or SMR gene in accordance with the invention may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated.

An expression vector of the invention preferably contains one or more selectable markers which permit easy selection of transformed hosts. For example, an expression vector my comprise a gene that confers antibiotic resistance (e.g., ampicillin, kanamycin, chloramphenicol or tetracycline resistance) to the recombinant host organism, e.g., a bacterial cell such as *E. coli*, that comprises the vector.

Suitable markers for other microbial host cells, such as yeast host cell are also well known and include, for example, ADE2, HIS3, LEU2, LYS2, MET3, TRP1, and URA3. Selectable markers for use in a filamentous fungal host include, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Markers for use in *Aspergillus* include the amdS and pyrG genes of *Aspergillus nidulans* ox *Aspergillus oryzae* and the bar gene of *Streptomyces hygroscopicus*. Markers for use in *Trichoderma* include bar and amdS.

An expression vector may additionally contain an element(s) that permits integration of the vector into the host's genome. In some embodiments, the expression vector may contain an element that permits autonomous replication of the vector in the cell independent of the genome.

Although any suitable expression vector may be used to incorporate the desired sequences, readily available bacterial expression vectors include, without limitation: plasmids, such as pSC1O1, pBR322, pBBR1MCS-3, pUR, pEX, pMR1OO, pCR4, pBAD24, pUC19; bacteriophages, such as M1 3 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

Expression vectors of the invention may be introduced into the host cell using any number of well-known methods, including calcium phosphate transfection, DEAE-Dextran mediated transfection, electroporation, via lipid complexes, or other common techniques.

Host Cells

Any number of microorganism can be transformed with an expression vector comprising a gene encoding a MFS or SMR protein in accordance with the invention. In some embodiments, the host cell is prokaryotic, such bacterial host cells. Examples of bacterial host cells include, without limitation, species assigned to the *Escherichia, Enterobacter, Azotobacter, Erwinia, Bacillus, Clostridium, Enterococcus, Lactobacillus, Lactococcu, Oceanobaciilus, Pseudomonas, Klebsiella, Proteus, Salmonella, Serratia, Shigella, Staphococcus, Strpeotcoccus, Streptomyces, Rhizobia, Vitreoscilla, Synechococcus, Synechocystis*, and *Paracoccus* taxonomical classes. In some embodiments, the prokaryotic host cells are *E. coli, Bacillus* sp. such as *Bacillus subtilis*. In some embodiments, the host cells are cyanobacteria.

In some embodiments, the host cell is a yeast. Examples of yeast host cells include *Candida, Hansenula, Kluyveromyces, Pichia, Saccharomyces, Schizosaccharomyces*, or *Yarrowia* host cells. In some embodiments, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In some embodiments, the yeast host cell is a *Kluyveromyces lactis* cell. In another embodiment, the yeast host cell is a *Yarrowia lipolytica* cell.

In other embodiments, the host cell is a filamentous fungal cell. In some embodiments, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Malbranchea, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell. For example, a filamentous fungal host cell may be an *Aspergillus awamori, Aspergillus fumigatus, Aspergillus foetidus, Aspergillus japonicus, Aspergillus nidulans, Aspergillus niger* or *Aspergillus oryzae* cell. In other embodiments, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In further embodiments, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Malbranchea cinnamomea, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma Iongibrachiatum, Trichoderma reesei*, or *Trichoderma viride* cell. In some embodiments, the filamentous fungal host cell is *Ustilago maydis*.

The host cells of the present invention may be genetically modified in that recombinant nucleic acids have been introduced into the host cells, and as such the genetically modified host cells do not occur in nature. The suitable host cell is one capable of expressing one or more nucleic acid constructs encoding one or more proteins for different functions.

In some embodiments, the host cell may be modified to express a tet repressor. The TetR family of transcription repressors is well known and various TetR sequences are available that can be employed to modify a host cell (see, e.g., Microbiol Mol Biol Rev. 69:326-356, 2005, which is incorporated by reference).

In some embodiments, the host cell naturally produces any of the proteins encoded by the polynucleotides of the invention. The genes encoding the desired proteins may be heterologous to the host cell or these genes may be endogenous to the host cell but are operatively linked to heterologous promoters and/or control regions which result in the higher expression of the gene(s) in the host cell. In other embodiments, the host cell does not naturally produce the desired proteins, and comprises heterologous nucleic acid constructs capable of expressing one or more genes necessary for producing those molecules.

Methods of Using Microorganism Engineered to Express MFS or SMR

The organisms modified in accordance with the invention can be used in saccharfication or fermentation reactions that employ IL-pretreated biomass. Biomass that is pretreated with an IL include, but is not limited to, a cellulose biomass, a hemicellulose biomass, a lignocellulose biomass and mixtures thereof. In some embodiments, the biomass pretreated with an IL is a lignocellulose biomass. The biomass may be pretreated using known processes (see, for example, Hermanutz, et al., *Macromol. Symp.* 262:23-27, 2008; PCT application PCT/US2012/042790).

Examples of ILs suitable for pretreatment of the biomass and for the hydrolysis of cellulose by cellulases include, but are not limited to 1-ethyl-3-methylimidazolium acetate (EMIM Acetate), 1-ethyl-3-methylimidazolium chloride (EMIM CI or ([C$_2$mim]Cl), 1-ethyl-3-methylimidazolium hydrogensulfate (EMIM HOSO$_3$), l-ethyl-3-methylimidazolium methylsulfate (EMIM MeOSO$_3$), 1-ethyl-3-methylimidazolium ethylsulfate (EMIM EtOSO$_3$), 1-ethyl-3-methylimidazolium methanesulfonate (EMIM MeSO$_3$), 1-ethyl-3-methylimidazolium tetrachloroaluminate (EMIM AICI4), 1-ethyl-3-methylimidazolium thiocyanate (EMIM SCN), 1-butyl-3-methylimidazolium acetate (BMIM Acetate), l-butyl-3-methylimidazolium chloride (BMIM CI), 1-butyl-3-methylimidazolium hydrogensulfate (BMIM HOSO$_3$), 1-butyl-3-methylimidazolium methanesulfonate (BMIM MeSO$_3$), 1-butyl-3-methylimidazolium methylsulfate (BMIM MeOSO$_3$), 1-butyl-3-methylimidazolium tetrachloroaluminate (BMIM AICI4), l-butyl-3-methylimidazolium thiocyanate (BMIM SCN), 1-ethyl-2,3-dimethylimidazolium ethylsulfate (EDIM EtOSO$_3$), Tris(2-hydroxyethyl) methylammonium methylsulfate (MTEOA MeOSO$_3$), 1-methylimidazolium chloride (MIM CI), 1-methylimidazolium hydrogensulfate (MIM HOSO$_3$), 1,2,4-trimethylpyrazolium methylsulfate, tributylmethylammonium methylsulfate, choline acetate, choline salicylate, and the like. The ionic liquid can comprises one or a mixture of the compounds. In some embodiments, the ionic liquid has an imidazolium cation. Additional suitable ILs are taught in U.S. Pat. No. 6,177,575. It will be appreciated by those of skill in the art that others ILs that will be useful in the process of the present invention are currently being developed or will be developed in the future, and the present invention contemplates their future use.

The pretreated biomass, e.g., the lignocellulose biomass, can be hydrolyzed enzymatically to break down, for example, hemicellulose and/or cellulose, into sugars. Typically, the pretreated biomass is subjected to the action of one, or several or all enzyme activities selected from a cellulase, a cellobiohydrolase, an endoglucanase, a glucanohydrolase, a protease, a pectinase, a xylanase, a lyase, a ferulic acid esterase, and a mannanase. In one embodiment, the pretreated biomass is subjected to the action of a cellulase, such as a thermostable cellulase. Cellulases suitable for use in the present invention are commercially available from, for example, Genencor (USA) and Novozymes (Europe). For instance, Novozyme has a number of different enzymes and enzyme complexes that are specifically designed to be useful for the hydrolysis of lignocellulosic materials. Examples include, but are not limited to, the following: NS50013, which is a cellulase; NS50010, which is a beta-glucosidase; NS22086, which is a cellulase complex; NS22086, which is a xylanase; NS22118, which is β-glucosidase; NS22119, which is an enzyme complex of carbohydrases, including arabinase, β-glucanase, cellulase, hemicellulase, pectinase, and xylanase; NS22002, which is a mixture of β-glucanase and xylanase; and NS22035, which is a glucoamylase. In addition, suitable thermostable cellulases are disclosed in PCT International Publication No. WO 2010/124266, the teachings of which are incorporated herein by reference. Other hydrolases suitable for hydrolyzing the pretreated biomass, i.e., the lignocellulosic material, will be known to those of skill in the art.

Hydrolysis may additionally be carried out by contacting the pretreated biomass with a microorganism genetically modified to express an MFS or SMR protein in accordance with the invention. Such an organism may be additionally modified to express one or more cellulases, or other enzymes involved in lignocellulose degradation.

A host cell engineered to express MFS or SMR may also be genetically modified to enhance other desired properties, such as improving growth, or modified to enhance yield of a desired product in a reaction that contains ionic liquids.

A host cell modified to express MFS or SMR may be used in any reaction for which it is desired to employ an organism that is tolerant to ionic liquids. For example, such a host cell can be used for producing any fermentation product or other product for which sugars obtained from hydrolysis of an ionic-liquid pretreated biomass can serve as a carbon source. Examples of products include, but are not limited to, alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); vitamins (e.g., riboflavin, B12, beta-carotene), fatty acids and fatty acid derivatives (as described, e.g., in PCT/US2008/068833); isoprenyl alkanoates (as described, e.g., PCT/US2008/068756, methyl butenol (as described, e.g., PCT/US2008/068831; fatty acid esters (as described, e.g., in PCT/US2010/033299), isoprenoid-based alternative diesel fuels (as described, e.g., in PCT/US2011/059784; a polyketide synthesized by a polyketide synthase, such as a diacid (see, e.g., PCT/US2011/061900), biofuels (see, e.g., PCT/US2009/042132) and alpha-olefins (see, e.g., PCT/US2011/053787). Both the enzymatic hydrolysis and subsequent steps to produce a desired organic compound can be carried out using procedures known to and used by those of skill in the art.

Methods of Identifying Genes that Confer Resistance to Ionic Liquids

A method of screening for genes that confer resistance to ionic liquids is taught in U.S. Patent Application Pub. No. 2014/0038848, which is incorporated by reference. The method comprises preparing a genomic library comprising the genome of a microorganism resistant to ionic liquids, e.g., *Enterobacter lignolyticus* SCF1 in a vector, e.g., a vector that accommodates large inserts, e.g., at least 30 kb, and introducing the library into the desired host cells. Typically, a low copy number vector is employed to enhance stability of the library. In some embodiments, the vector is a fosmid vector or bacterial artificial chromosome that contains an f-factor origin replication. These are derived from *E. coli* f-factor which is able to stably integrate large segments of genomic DNA. When integrated with DNA from a mixed uncultured environmental sample, this makes it possible to achieve large genomic fragments in the form of a stable library. The vector may contain additional sequences such as selectable markers. The library can then be screened for colonies that are resistant to ionic liquids by plating the library onto media containing an ionic liquid of interest, e.g., [C₂mim]Cl, at a desired concentration, e.g., from about 1% to about 6%. Colonies that exhibit relatively fast growth can then be selected and evaluated to determine gene(s) present in the clone and further tested to determine whether the gene can confer resistance to an ionic liquid to host cells transformed with an expression vector that expresses the gene. In some embodiments, the copy number may be amplified to facilitate isolated the DNA of interest.

In some embodiments, the library comprises genomic inserts from more than one microorganism. For example, genomic DNA can be isolated from an environmental sample and a library can be screened as described above. The identity of the microorganisms from which the genomic DNA is isolated need not be known.

YDR090C Proteins

Another aspect of the invention is the *S. cerevisiae* YDR090C protein. Where this present specification refers to a MFS or SMR protein, that term is meant also include the *S. cerevisiae* YDR090C protein.

For example, in one aspect, the invention provides a recombinant microorganism having resistance to ionic liquids, e.g., an ionic liquid where the anion is Cl⁻ or acetate, wherein the microorganism comprises a heterologous gene encoding a protein or polypeptide having at least 70% identity, or at least 75%, 80%, or 85% identity, to SEQ ID NO:22. In some embodiments, the polypeptide has at least 90% identity, or at least 95% identity, to SEQ ID NO:22. In some embodiments, the polypeptide comprises SEQ ID NO:22. In some embodiments, the heterologous gene is operably linked to a tet repressor sequence. In some embodiments, the microorganism is also genetically modified to express a tet repressor protein that binds to the tet repressor sequence. In some embodiments, the microorganism is a bacteria, such as *Escherichia coli*. In other embodiments, the microorganism is a yeast or filamentous fungi. In some embodiments, the heterologous gene encoding the polypeptide is integrated into the genome of the microorganism. In some embodiments, the heterologous gene encoding the polypeptide is present on an extrachromosomal autonomously replicating sequence present in the microorganism.

In a further aspect, the invention provides a method of modifying a microorganism to have resistance to ionic liquids, e.g., ionic liquids where the anion is Cl⁻ or acetate, the method comprising introducing an expression cassette into the microorganism, wherein the expression cassette comprises a gene encoding a protein or polypeptide that has at least 70% identity, or at least 75%, 80%, or 85% identity, to SEQ ID NO:22. In some embodiments, the polypeptide has at least 90% identity, or at least 95% identity, to SEQ ID NO:22. In other embodiments the polypeptide comprises SEQ ID NO:22. In some embodiments, the heterologous gene is operably linked to a tet repressor sequence. In some embodiments, the method further comprises engineering the microorganism to express a tet repressor that binds to the tet repressor sequence. In some embodiments, the method comprises engineering bacteria, such as *Escherichia coli*. In other embodiments, the method comprises engineering a yeast or filamentous fungi. In some embodiments, the method comprises integrating the heterologous gene encoding the polypeptide into the genome of the microorganism.

In a further aspect, the invention provides a composition comprising a microorganism of the invention comprising a heterologous gene that is capable of expressing a YDR090C polypeptide. In some embodiments, the composition is a reaction mixture that comprises an ionic liquid and the microorganism of the invention. In some embodiments, the reaction mixture further comprises biomass.

In an additional aspect, the invention provides a method of increasing the yield of soluble sugar from a biomass, the method comprising incubating biomass pretreated with a microorganism genetically modified to comprise a heterologous YDR090C gene in an enzymatic hydrolysis reaction. The invention additionally provides a method of increasing the yield from a reaction in which soluble sugars are a source of carbon, e.g., a fermentation reaction that produces a biofuel, such as an alcohol, the method comprising incubating biomass pretreated with ionic liquid with a microorganism of the invention in a reaction.

*Salmonella* MFS SmvA Pump and SmvR Regulator

The amino acid sequence of the *Salmonella* MFS Pump, SmvA Pump (found at the website for ncbi.nlm nih gov/protein/AAL20492.1) is:

```
                                                              (SEQ ID NO: 1)
  1 mfrgwltlvi ivlvyipvai datvlhvaap tlsmtlgasg nellwiidiy slvmagmvlp 61 mgalgdrigf krllmlggtl fglaslaaaf shtaswliat rvllaigaam ivpatlagir 121 atfceekhrn malgvwaavg sggaafgpli ggillehfyw gsvflinvpi vlvvmgltar 181 yvprgagrrd qplnlghavm liiailllvy saktalkghl slwvisftll tgalllglfi 241 rtqlatsrpm idmrlfthri ilsgvvmamt amitivgfel lmagelqfvh glspyeagvf 301 mlpvmvasgf sgpiagvlvs rlglrlvatg gmalsalsfy glamtdfstq qwqawglmal 361 lgfsaasall astsaimaaa paekaaaaga ietmayelga glgiaifgll lsrsfsasir 421 lpagleagei arasssmgea vqlanslppt qgqaildaar hafiwshsva lssagsmlll 481 lavgmwfsla kaqrr
```

The amino acid sequence of the *Salmonella* MFS Pump, SmvR Regulator (found at the website for ncbi.nlm nih gov/protein/AAL20493.1) is:

```
                                                       (SEQ ID NO: 2)
  1 msylnrderr evilqaamrv alaegfaamt vrriaseadv aagqvhhhfs sagelkalaf 61 vhlirtllda gqvpppatwr arlhamlgse dggfepyikl wreaqiladr dphirdayll 121 tmqmwheetv tiieqgkqag eftftanatd iawrlialvc gldgmyvlgi pemadpafkf 181 hldrmitlel fa
```

SMR Proteins

The amino acid sequence of the *Bacillus licheniformis* Pump (from Z98 environmental isolate has the same DNA/protein sequence as the type strain (ATCC 14580=DSM13)), YkkC (found at the website for ncbi.nlm nih gov/protein/AAL20493.1) is:

```
                                                       (SEQ ID NO: 3)
 1 mrwgsvilaa lfeigwvmgl khadsalewi ctaaavvmsf yilvkagekl pvgtvyavft 61 glgtagtvvc eialfnepan iaklaligvl lcgviglklv tneekgeas
```

The amino acid sequence of the *Bacillus licheniformis* Pump (from Z98 environmental isolate has the same DNA/protein sequence as the type strain (ATCC 14580=DSM13)), YkkD (found at the website for ncbi.nlm.nih gov/protein/AAU40314.1) is:

```
                                                       (SEQ ID NO: 4)
 1 mewicliaag ilemlgvtmm nqfhkdkrvr wiflliigfa asffllslam etlpmgtaya 61 vwtgigtvgg alvgilfyge pkdgkriffi alilgsavgl klis
```

The promoter preceding these *Bacillus licheniformis* genes may encode an IL-sensing riboswitch region. The environmental Z98 isolate's promoter is similar to, but slightly shorter than, the promoter in the type strain.

The amino acid sequence of the *Bacillus cereus* JP5 Pump A1 (first member of operon) is:

```
                                            (SEQ ID NO: 5)
MKNRAWLYVILTCIFEIFWVFGFNTADTWWHWIIILGVIAVDFHFLSKA

CEHLATGTVYAIFAGAGTVGTFLMDVFLFGGSFSVGKLFFIVMVVAGV

IGLKLADNKEESVEGAA*
```

The amino acid sequence of the *Bacillus cereus* JP5 Pump A2 (second member of operon) is:

```
                                            (SEQ ID NO: 6)
MGWFFVFCAAISEIVGVIGLKMYSKDKTLANGALYIGGFATSFAFLYTSF

LFLQVSVAYAVWIGIGTAGAVLLNMFLFGESKSKARIISVALIVCGVTGL

KALS*
```

The amino acid sequence of the *Bacillus cereus* JP5 Pump regulator (repressor) is:

```
                                            (SEQ ID NO: 7)
MMNKKEKIVYAAIEVFQEKGVEKTKISDIVKLAGIAQGTFYLYFPSKLSV

MPAIAEVMVEKMILAVKEKVQNDAPFSSKVTQVIDAVFHFIAEYREIQAL

MYAGLASTEHIKEWEAVYEPLYMWLSEFLNEAKEAGEIRDSVHAERTAKL

FIALVESAAEQVYLYDHKDDEQVELQKAEVLDFLTHALHIKK* m
```

The amino acid sequence of the *Bacillus cereus* JP5 Pump regulator (acetyl transferase) is:

```
                                            (SEQ ID NO: 8)
MNICNAVTSDVKEIYSLIEVYAKEGVVLPRSLLSLYQYLQCLYVVKEEE

KIVGVAGLHVLGEDLAEVRSLVVSHIYAGKGIGRMLVNHVINEAAKIKV

SRVISLTYETEFFQKCGFDFVNRDALPEKVWIDCRHCPKVDYCDEVAM

IRYVG*
```

The amino acid sequence of the *Bacillus thuringiensis* BGSC 4A11^T Pump A1 (first member of operon) (found at the website for ncbi.nlm.nih.gov/protein/228821582) is:

(SEQ ID NO: 9)
```
  1 mrgmknrawl yviltcifei fwvfgfntad twwhwiiilg viavdfhfls kacehlatgt
 61 vyavfagagt vgtflmdvfl fggsfsagkl ffilmvvagv iglkladnke etvegaa
```

The amino acid sequence of the *Bacillus thuringiensis* BGSC 4A11^T Pump A2 (second member of operon) (found at the website for ncbi.nlm.nih.gov/protein/228821583) is:

(SEQ ID NO: 10)
```
  1 mgwffvfcaa iseivgvigl kmyskdktla ngaiyiggfa tsfaflytsf lflgvsvaya
 61 vwigigtaga vllnmflfge skskariisv flivcgvtgl kals
```

The amino acid sequence of the *Bacillus thuringiensis* BGSC 4A11^T Pump A Regulator (repressor) (found at the website for ncbi.nlm nih gov/protein/228821584) is:

(SEQ ID NO: 11)
```
  1 mmnkkekivy aaievfgekg vektkisdiv klagiaggtf ylyfpsklsv mpaiaevmve
 61 kmilavkekv gkdvpfsnkv agvidavfhf ieeyreigal myaglasteh ikeweavyep
121 lymwlsefls eakeageird svhaertakl fialvesaae qvylydh kdd egvelqkaev
181 ldflthalhi kk
```

The amino acid sequence of the *Bacillus thuringiensis* BGSC 4A11^T Pump A Possible Regulator (acetyl transferase) (found at the website for ncbi.nlm.nih.gov/protein/228821578) is:

(SEQ ID NO: 12)
```
  1 mtsdvkeiyn lievyakegv vlprsllsly qylqclyvmk ederivgvag lhvlgedlae
 61 irslvvshty agkgigrmlv nhvmeeatki nvrrvislty etvffqkcgf dfvnketlpe
121 kvwidcrhcp kvdycdevam vryvg
```

The amino acid sequence of the *Bacillus cereus* JP5 Pump B1 (first member of operon) is:

(SEQ ID NO: 13)
MAWIYVILAGIIEIFWVIGLKHAEAPLEWAGVALLITISFVLLFRAYKDL
PVGTVYAVFTGIGAGGIVLTEIFVFGEPFSIVKVLLIGLIFFGVIGLKRV
TEEKEAKEAA*

The amino acid sequence of the *Bacillus cereus* JP5 Pump B2 (second member of operon) is:

(SEQ ID NO: 14)
MAWVFLILAGICEIIGVLFMKVATEKKGWAPKVILIANFGVSFFFLSLAM
NTLPMGTAYAIWTGIGTAGSALLGILIFRESADWRRLAFLSCILCGAVGL
KLLS*

The amino acid sequence of the *Bacillus cereus* JP5 Pump B regulator (repressor) is:

(SEQ ID NO: 15)
MTANRIKAVALSHFARYGYEGTSLANIAQEVGIKKPSIYAHFKGKEELYF
TCLESALQKDLQSFTGDIEKFSNSSTEELLLQLLKGYAKRFGESEESMFW
LRTSYFPPDAFREQIINKANVHIENVGKLLFPVFKRASEQDELHNIEVKD
ALEAFLCLLDGLMVELLYAGLNRFETRLDASWKVFWRGLSN*

The amino acid sequence of the *Bacillus thuringiensis* BGSC 4A11^T Pump B1 (first member of operon) (found at the website for ncbi.nlm.nih.gov/protein/228818299) is:

```
                                                    (SEQ ID NO: 16)
  1 mawiyviiag iieifwvigl kkaeaplewa gvallitisf vllfraykdl pvgtvyavft 61 gigaggivlt eififgepfs ivkvlligli ffgviglkrv teekeakeaa
```

The amino acid sequence of the *Bacillus thuringiensis* BGSC 4A11$^T$ Pump B2 (second member of operon) (found at the website for ncbi.nlm.nih.gov/protein/228818300) is:

```
                                                    (SEQ ID NO: 17)
  1 mawvflilag iceiigvlfm kvatekkgwa pkvilianfg vsffflslam ntlpmgtaya 61 iwtgigtags allgilifre sadwrrlafl scilcgavgl klls
```

The amino acid sequence of the *Bacillus thuringiensis* BGSC 4A11$^T$ Pump B Regulator (repressor) (found at the website for ncbi.nlm nih gov/protein/228818298) is:

```
                                                    (SEQ ID NO: 18)
  1 mkmtanrika valshfaryg yegtslania qevgikkpsi yahfkgkeel yficlesalq 61 kdlqsftgdi esfsnsstee lllkllkgya krfgeseesm fwlrtsyfpp dafreqiink 121 anvhienvgk llfpvfkras eqdelhniev kdaleaflcl ldglmvelly aglnrfetrl 181 daswkvfwrg lsn
```

The amino acid sequence of the *E. coli* EmrE (found at the website for ncbi.nlm.nih.gov/protein/AAC73644.1) is:

```
                                                    (SEQ ID NO: 19)
  1 mnpyiylgga ilaevigttl mkfsegftrl wpsvgtiicy casfwllaqt layiptgiay 61 aiwsgvgivl islIswgffg qrldlpaiig mmlicagvli inllsrstph
```

The amino acid sequence of the *E. coli* SugE (found at the website for ncbi.nlm.nih.gov/protein/AAC77108.2) is:

```
                                                    (SEQ ID NO: 20)
  1 mswiilviag llevvwavgl kythgfsrlt psvitvtami vsmallawam kslpvgtaya 61 vwtgigavga aitgivllge sanpmrlasl alivlgiigl klsth
```

Yeast MFS Protein

The amino acid sequence of the *S. cerevisiae* SGE1 (found at the website for yeastgenome.org/cgi-bin/locus.fpl?locus=S000006402) is:

```
                                                    (SEQ ID NO: 21)
  1 MKSTLSLTLC VISLLLTLFL AALDIVIVVT LYDTIGIKFH DFGNIGWLVT

51 GYALSNAVFM LLWGRLAEIL GTKECLMISV IVFEIGSLIS ALSNSMATLI

101 SGRVVAGFGG SGIESLAFVV GTSIVRENHR GIMITALAIS YVIAEGVGPF

151 IGGAFNEHLS WRWCFYINLP IGAFAFIILA FCNTSGEPHQ KMWLPSKIKK

201 IMNYDYGELL KASFWKNTFE VLVFKLDMVG IILSSAGFTL LMLGLSFGGN

251 NFPWNSGIII CFFTVGPILL LLFCAYDFHF LSLSGLHYDN KRIKPLLTWN

301 IASNCGIFTS SITGFLSCFA YELQSAYLVQ LYQLVFKKKP TLASIHLWEL

351 SIPAMIATMA IAYLNSKYGI IKPAIVFGVL CGIVGSGLFT LINGELSQSI

401 GYSILPGIAF GSIFQATLLS SQVQITSDDP DFQNKFIEVT AFNSFAKSLG
```

```
451 FAFGGNMGAM IFTASLKNQM RSSQLNIPQF TSVETLLAYS TEHYDGPQSS

501 LSKFINTAIH DVFYCALGCY ALSFFFGIFT SSKKTTISAK KQQ*
```

In some embodiments, the yeast MFS protein has the amino acid sequence of *S. cerevisiae* SGE1 with the exception of having the following amino acid substitution: S282P, S284L, or both.

Yeast YDR090C Protein

The amino acid sequence of the *S. cerevisiae* YDR090C (found at the website for yeastgenome.org/cgi-bin/locus.fpl?locus=ydr090C) is:

```
                                                 (SEQ ID NO: 22)
  1 MISEKAATAL ATIATVCWCV QLIPQIIYNW KKKDCTGLPP LMMFLWVVSG

51 IPFAIYFCVS KGNVILQVQP HLFMFFCSIS FVQSCYYPPI SMARSKIVMI

101 VAAIIAADVG MEVGFILWLR PLYEKGVKWP DLIFGISASV LLAVGLLPPY

151 FELAKRKGRV IGINFAFLFI DSLGAWLSII SVILGNMDIM GIILYSIVAG

201 MELGIFASHF IWWCRFRFLA KGNTFDEESG QAQKEEPDEK IEQDISKSDR

251 NVTNYNLDNC SIPDDASSFA DDFNIYDSTD GGTLSRAQTL HAVHGVVVRT

301 DPDRYSRLSV *
```

The present invention provides for the following:

A recombinant microorganism having resistance to ionic liquids, wherein the microorganism comprises a heterologous gene encoding a yeast Major Facilitator Superfamily (MFS), or a *Salmonella* MFS SmvA Pump or SmvR Regulator, polypeptide operably linked to a promoter, wherein the polypeptide has at least 70% identity to one amino acid sequence selected from the group consisting of SEQ ID NOs:1, 2, and 21. In some embodiments, the polypeptide has at least 90% identity to one amino acid sequence selected from the group consisting of SEQ ID NOs:1, 2, and 21. In some embodiments, the polypeptide comprises one amino acid sequence selected from the group consisting of SEQ ID NOs:1, 2, and 21, SEQ ID NO:21 with the following amino acid substitution S282P, S284L, or both. In some embodiments, the heterologous gene is operably linked to a tet repressor sequence. In some embodiments, the microorganism is a bacteria. In some embodiments, the bacteria is *Escherichia coli*. In some embodiments, the microorganism is a yeast or filamentous fungi. In some embodiments, the anion of the ionic liquid is Cl— or acetate. In some embodiments, the heterologous gene encoding the polypeptide is on a vector or is integrated into the genome of the microorganism.

A method of modifying a microorganism to have resistance to ionic liquids, the method comprising introducing an expression cassette into the microorganism, wherein the expression cassette comprises a gene encoding a yeast MFS, or a *Salmonella* MFS SmvA Pump or SmvR Regulator, polypeptide that has at least 70% identity to one amino acid sequence selected from the group consisting of SEQ ID NOs:1, 2, and 21. In some embodiments, the polypeptide has at least 90% identity to one amino acid sequence selected from the group consisting of SEQ ID NOs:1, 2, and 21. In some embodiments, the polypeptide comprises one amino acid sequence selected from the group consisting of SEQ ID NOs:1, 2, and 21. In some embodiments, the heterologous gene is operably linked to a tet repressor sequence. In some embodiments, the microorganism is a bacteria. In some embodiments, the bacteria is *Escherichia coli*. In some embodiments, the microorganism is a yeast or filamentous fungi. In some embodiments, the anion of the ionic liquid is Cl— or acetate. In some embodiments, the heterologous gene encoding the polypeptide is on a vector or is integrated into the genome of the microorganism.

A method of increasing the yield of soluble sugar from a biomass, the method comprising incubating biomass pretreated with a recombinant microorganism having resistance to ionic liquids of the present invention in an enzymatic hydrolysis reaction.

A method of increasing the yield from a reaction in which soluble sugars are a source of carbon, the method comprising incubating biomass pretreated with ionic liquid with a recombinant microorganism having resistance to ionic liquids of the present invention. In some embodiments, the biomass is incubated with the microorganism in a fermentation reaction that produces an alcohol.

A composition comprising biomass pretreated with ionic liquid and a recombinant microorganism having resistance to ionic liquids of the present invention.

A recombinant microorganism having resistance to ionic liquids, wherein the microorganism comprises a heterologous gene encoding a Small Multidrug Resistance Family (SMR) polypeptide operably linked to a promoter, wherein the polypeptide has at least 70% identity to one amino acid sequence selected from the group consisting of SEQ ID NOs:3-20. In some embodiments, the polypeptide has at least 90% identity to one amino acid sequence selected from the group consisting of SEQ ID NOs:3-20. In some embodiments, the polypeptide comprises one amino acid sequence selected from the group consisting of SEQ ID NOs:3-20. In some embodiments, the heterologous gene is operably linked to a tet repressor sequence. In some embodiments, the microorganism is a bacteria. In some embodiments, the bacteria is *Escherichia coli*. In some embodiments, the microorganism is a yeast or filamentous fungi. In some embodiments, the anion of the ionic liquid is Cl— or acetate. In some embodiments, the heterologous gene encoding the polypeptide is on a vector or is integrated into the genome of the microorganism.

A method of modifying a microorganism to have resistance to ionic liquids, the method comprising introducing an expression cassette into the microorganism, wherein the expression cassette comprises a gene encoding a SMR polypeptide that has at least 70% identity to one amino acid sequence selected from the group consisting of SEQ ID NOs:3-20. In some embodiments, the polypeptide has at least 90% identity to one amino acid sequence selected from the group consisting of SEQ ID NOs:3-20. In some embodiments, the polypeptide comprises one amino acid sequence selected from the group consisting of SEQ ID NOs:3-20. In some embodiments, the heterologous gene is operably linked to a tet repressor sequence. In some embodiments, the microorganism is a bacteria. In some embodiments, the bacteria is *Escherichia coli*. In some embodiments, the microorganism is a yeast or filamentous fungi. In some embodiments, the anion of the ionic liquid is Cl— or acetate. In some embodiments, the heterologous gene encoding the polypeptide is on a vector or is integrated into the genome of the microorganism.

A method of increasing the yield of soluble sugar from a biomass, the method comprising incubating biomass pretreated with a recombinant microorganism having resistance to ionic liquids of the present invention in an enzymatic hydrolysis reaction.

A method of increasing the yield from a reaction in which soluble sugars are a source of carbon, the method comprising incubating biomass pretreated with ionic liquid with a recombinant microorganism having resistance to ionic liquids of the present invention. In some embodiments, the biomass is incubated with the microorganism in a fermentation reaction that produces an alcohol.

A composition comprising biomass pretreated with ionic liquid and a recombinant microorganism having resistance to ionic liquids of the present invention.

A recombinant microorganism having resistance to ionic liquids, wherein the microorganism comprises a heterologous gene encoding a *Saccharomyces cerevisiae* YDR090C polypeptide operably linked to a promoter, wherein the polypeptide has at least 70% identity to SEQ ID NO:22. In some embodiments, the polypeptide has at least 90% identity to SEQ ID NO:22. In some embodiments, the polypeptide comprises SEQ ID NO:22. In some embodiments, the heterologous gene is operably linked to a tet repressor sequence. In some embodiments, the microorganism is a bacteria. In some embodiments, the bacteria is *Escherichia coli*. In some embodiments, the microorganism is a yeast or filamentous fungi. In some embodiments, the anion of the ionic liquid is Cl— or acetate. In some embodiments, the heterologous gene encoding the polypeptide is on a vector or is integrated into the genome of the microorganism.

A method of modifying a microorganism to have resistance to ionic liquids, the method comprising introducing an expression cassette into the microorganism, wherein the expression cassette comprises a gene encoding a *Saccharomyces cerevisiae* YDR090C polypeptide that has at least 70% identity to SEQ ID NO:22. In some embodiments, the polypeptide has at least 90% identity to SEQ ID NO:22. In some embodiments, the polypeptide comprises SEQ ID NO:22. In some embodiments, the heterologous gene is operably linked to a tet repressor sequence. In some embodiments, the microorganism is a bacteria. In some embodiments, the bacteria is *Escherichia coli*. In some embodiments, the microorganism is a yeast or filamentous fungi. In some embodiments, the anion of the ionic liquid is Cl— or acetate. In some embodiments, the heterologous gene encoding the polypeptide is on a vector or is integrated into the genome of the microorganism.

A method of increasing the yield of soluble sugar from a biomass, the method comprising incubating biomass pretreated with a microorganism having resistance to ionic liquids of the present invention in an enzymatic hydrolysis reaction.

A method of increasing the yield from a reaction in which soluble sugars are a source of carbon, the method comprising incubating biomass pretreated with ionic liquid with a microorganism having resistance to ionic liquids of the present invention. In some embodiments, the biomass is incubated with the microorganism in a fermentation reaction that produces an alcohol.

A composition comprising biomass pretreated with ionic liquid and a microorganism having resistance to ionic liquids of the present invention.

The invention having been described, the following examples are offered to illustrate the subject invention by way of illustration, not by way of limitation.

EXAMPLE 1

Ionic Liquid Tolerance in Microbes

Cheap, abundant sugar is an absolute requirement for the commercial viability of microbially produced biofuels. Ionic liquid (IL) treatment is among the best and most environmentally friendly methods for preparing plant biomass for enzymatic breakdown into sugars for microbial growth. However, residual ILs present in these sugars inhibit both *Escherichia coli* and *Saccharomyces cerevisiae* growth, thereby preventing efficient biofuel production. To understand and overcome this growth inhibition, we have isolated several environmental microbes—Gram-negative and Gram-positive bacteria and fungi—that can tolerate a common imidazolium-based IL at concentrations well above those that are toxic to our biofuel-producing strains. Using metagenomic screening strategies, we have identified two families of bacterial pumps, and one fungal pump, that provide ionic liquid resistance to *E. coli* and *S. cerevisiae*, respectively. These bacterial pumps occur in tandem with transcriptional regulators that appear to adjust pump levels in response to changing IL concentrations. Further studies are aimed at fine tuning these pumps and their regulators for use in biofuel-producing *E. coli*. The discovery of IL-tolerant communities of microbes has overcome a major hurdle in the use of cellulose-solubilizing solvents, and will advance our progress towards readily and economically converting lignocellulose biomass to biofuels and renewable chemicals.

This study describes six ionic liquid tolerance genes that are shown to operate in bacteria and two genes that are shown to operate in yeast. The bacterial genes consist of an MFS pump and five pumps of the Small Multidrug Resistance (SMR) family, that demonstrated to protect *E. coli* from [C2mim]-based ILs. The MFS pump is the *Salmonella* protein SmvA, which, along with its regulator SmvR, is capable of protecting *E. coli* from harmful levels of [C2mim]Cl and [C2mim][OAc]. The *Salmonella* homologue of *Enterobacter*'s EilA, SmvA is able to secrete [C2mim]Cl and [C2mim][OAc]. The yeast genes are the *Saccharomyces cerevisiae* MFS pump, SGE1 (YPR198W), and *S. cerevisiae* YDR090C.

Bacterial Genes

Three of our new SMR pumps come from members of the genus *Bacillus*. One is from an environmental *B. licheniformis* isolate, named Z98, and is produced by the protein products of the genes ykkC and ykkD The second and third pumps come from *B. cereus* isolate JP5. Each of these pumps is similarly comprised of two SMR proteins. Pumps from related bacilli work with comparable activity. Specifically, the YkkCD pump homologue from type strain of *Bacillus licheniformis* strain and the homologues of the *B. cereus* pumps with those from the type strain of *Bacillus thuringiensis* are tested.

Another two bacterial [C2mim]-resistance pumps are the SMR proteins SugE and EmrE from *E. coli*. Although not normally induced, when either sugE or emrE is expressed from an inducible promoter, it confers IL resistance.

Different IL-pump regulatory mechanisms are also identified. The *B. licheniformis* pump's expression is predicted to be regulated by a riboswitch that detects ILs directly. As for the MFS pump EilA, which is regulated by the TetR-family repressor EilR, the *B. cereus* pumps appear to be regulated by TetR-family repressors. Interestingly, one of these TetR family repressors appears to require the joint action of a neighboring protein, and is predicted to be an acetyl transferase, in order to derepress pump expression.

Yeast Genes

Two yeast genes of interest are identified from two highly ionic liquid tolerant strains of *S. cerevisiae*, the strains 378604X and YS9. Expression of SGE1 from 378604X leads to high IL tolerance in laboratory *S. cerevisiae* strains. However, expression of SGE1 from either YS9 or our "laboratory" *S. cerevisiae* strain, the S288C derivative, BY4741, also increase ionic liquid resistance. Similar results are observed for the other yeast gene of interest, YDR090C. In other words, YDR090C sourced from all 3 strains induced a healthy boost in ionic liquid tolerance, but, for YDR090C, it is believed that YS9 may be the best source of the gene.

Possession of extra copies of these genes leads to increased protection, but it is also believed that specific changes in the amino acid sequences of SGE1 and YDR090C proteins in the ionic liquid tolerance strains, or nucleotide sequences in the promoters of these genes in these strains, may lead to especially increased tolerance in these strains.

Finally, there is indication that these genes are be more effective when other nearby genomic regions are included with them. These include, for SGE1, the ~17 gene region between YPR182W and YPR201W and, for YDR090C, the region encompassing the genes STN1, RRP8, TVP23, AFRI, SSS1, RRP1, SLUT, and YDR089W, as well as the genomic stretches that punctuate these genes.

FIG. 2 shows screening for IL tolerance in *E. coli*. FIG. 3 shows identifying bacterial IL tolerance genes. FIG. 4 shows pump expression rescues *E. coli* growth in IL. *E. coli* cells carrying MFS or SMR pumps driven by an IPTG-inducible promoter were grown in 125 mM (1.8%) [C2mim] Cl and 100 μM IPTG. Many identified pump genes appear beside genes for TetR-type regulatory proteins. FIG. 5 shows identifying yeast IL tolerance genes. *S. cerevisiae* cells, either wildtype or carrying low-copy number fosmids, were grown in 125 mM (2.1%) [C2mim][OAc] in SC-URA at pH 5. FIG. 6 shows the IL-inducible repressor EiLR regulates efflux pump expression in *E. coli*. Panel A shows EilR repressor is IL responsive: *E. coli* cells expressing MFS pump-GFP fusion from native gene cassette. Upper: no [C2mim]Cl. Lower: 4% [C2mim]Cl. Panel B shows EilR enables dynamically pump expression: Single cell fluorescence of *E. coli* expressing MFS pump-GFP fusion. Panel C shows EilR increases cell growth: Maximum growth rates of *E. coli* expressing MFS pump constitutively from native eilA promoter or under the control of EilR.

These findings are novel or unexpected for a number of reasons:

(1) This is the first report of specific genes that lead to ionic liquid tolerance in yeast.

(2) These results show that an entirely different class of transporters, SMR pumps are capable of the same activity. Similarly, the yeast gene YDR090C, is of unknown function, but has been implicated in possibly protecting the integrity of the yeast vacuole. This, if true, would also be a novel protective IL protection mechanism.

(3) It is surprising that pumps from bacilli, which are Gram-positive, work so well in the membranes of *E. coli*, which are Gram-negative organisms, as these two classes of bacteria have very different membranes.

(4) Unlike the other IL pumps, SugE and EmrE are endogenous to *E. coli*, and SGE1 and YDR090C are endogeonous to *S. cerevisiae*. Accordingly, they may prove to be most effective at protecting their native hosts without interfering with the cells' other activities.

(5) MFS and SMR pumps may not be very selective about the compounds they export. The regulators that govern their expression, however, are selective about what they respond to. In addition to several new pumps, we have also identified new IL-pump regulatory mechanisms. These identifications may prove even more useful than the pump library for engineering bacterial growth on IL-treated biomass. While pumps may work equally well with different ILs, regulators may be more specialized.

CONCLUSION

Targeted, functional screening of DNA from environmental microorganisms is a powerful approach for the discovery of mechanisms underpinning phenotypes such as bacterial resistance to inhibitory compounds. Such mechanisms, which include substrate specific regulators, remain fully functional when transferred to industrial host organisms, such as *E. coli* and can be a powerful tool for strain engineering. The discovery and investigation of IL-tolerant communities of microbes has overcome a major hurdle in the use of cellulose-solubilizing solvents, and advances our progress towards readily and economically converting lignocellulose biomass to biofuels and renewable chemicals.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What we claim is:

1. A culture medium comprising an ionic liquid and a recombinant microorganism, wherein the microorganism comprises a heterologous gene encoding a polypeptide operably linked to a promoter, wherein the polypeptide has at least 95% identity to one amino acid sequence selected from the group consisting of SEQ ID NOs:1 and 21, and the expression of the polypeptide confers to the microorganism resistance to the concentration of the ionic liquid in the culture medium.

2. The culture medium of claim 1, wherein the polypeptide has at least 99% identity to one amino acid sequence selected from the group consisting of SEQ ID NOs:1 and 21.

3. The culture medium of claim 1, wherein the polypeptide comprises at least 95% identity to SEQ ID NO:21 and the polypeptide comprises a proline at a position corresponding to position 282 of SEQ ID NO:21, a leucine at a position corresponding to position 284 of SEQ ID NO:21, or both.

4. The culture medium of claim 1, wherein the heterologous gene is operably linked to a tet repressor sequence.

5. The culture medium of claim 1, wherein the microorganism is a bacteria.

6. The culture medium of claim 5, wherein the bacteria is *Escherichia coli*.

7. The culture medium of claim 1, wherein the microorganism is a yeast or filamentous fungi.

8. The culture medium of claim 1, wherein the anion of the ionic liquid is Cl⁻ or acetate.

9. The culture medium of claim 1, wherein the heterologous gene encoding the polypeptide is on a vector or is integrated into the genome of the microorganism.

10. The culture medium of claim 1, wherein the culture medium further comprises a biomass.

11. The culture medium of claim 1, wherein the culture medium comprises about 1% to about 20% of the ionic liquid.

\* \* \* \* \*